(12) United States Patent
Zhu et al.

(10) Patent No.: US 6,936,464 B1
(45) Date of Patent: Aug. 30, 2005

(54) IMMUNE RESPONSES TO FUSION PROTEINS

(75) Inventors: Delin Zhu, Southampton (GB); Robert E Hawkins, Cambridge (GB); Stephen J. Russell, Cambridge (GB); Freda K. Stevenson, Southampton (GB); Gregory P Winter, Cambridge (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 08/896,535

(22) Filed: Jul. 18, 1997

Related U.S. Application Data

(63) Continuation-in-part of application No. 08/411,622, filed on Jun. 14, 1995, now abandoned.

(30) Foreign Application Priority Data

| | | |
|---|---|---|
| Oct. 2, 1992 | (GB) | 9220808 |
| Oct. 4, 1993 | (WO) | PCT/GB93/02054 |
| Jun. 14, 1995 | (WO) | 08411622 |

(51) Int. Cl.$^7$ .................. C12N 15/63; C12N 15/00; C12N 5/00; A61K 48/00
(52) U.S. Cl. .................. 435/320.1; 435/455; 435/4; 435/325; 514/44
(58) Field of Search .................. 435/4, 455, 325, 435/320.1; 514/44

(56) References Cited

U.S. PATENT DOCUMENTS

| | | | |
|---|---|---|---|
| 5,580,859 A | 12/1996 | Felgner et al. | 514/44 |
| 5,589,466 A | 12/1996 | Felgner et al. | 514/44 |
| 5,910,488 A | 6/1999 | Nabel et al. | 514/44 |
| 6,214,804 B1 | 4/2001 | Felgner et al. | 514/44 |
| 6,413,942 B1 | 7/2002 | Felgner et al. | 514/44 |

FOREIGN PATENT DOCUMENTS

| | | |
|---|---|---|
| WO | 90 11092 | 10/1990 |
| WO | WO 90/11092 | 10/1990 |
| WO | 92 01047 | 1/1992 |

OTHER PUBLICATIONS

Ross et al. Human Gene Therapy, vol. 7, 1781–1790, Sep. 1996.*
Orkin et al. "Report and Recommendations of the panel to assess the NIH investment in research on gene therapy", Dec. 1995.*
Marshall et al. Science, vol. 269, 1050–1055, Aug. 1995.*
Verma et al. Science, vol. 389, 239–242, Sep. 1997.*
Marshall et al. Science, vol. 269, 1050–1055, Aug. 1995.*
Verma et al. Science, vol. 389, 239–242, Sep. 1997.*
Hawkins et al. (1993) Br. J. Cancer, vol. 67 (Suppl. XX):13.*
Yu et al. (1994) Int. J. Cancer, vol. 56, 244–248.*
Ross et al. Human Gene Therapy, vol. 7, 1781–1790, Sep. 1996.*
Orkin et al. "Report and Recommendations of the panel to assess the NIH investment in research on gene therapy", Dec. 1995.*
Hawkins et al (1992) Cell selection strategies for making antibodies from variable gene libraries: trapping the memory pool, European Journal of Immunology, vol 22, pp. 867–870.
Campbell et al (1987) "Idiotype vaccination against murine B cell lymphoma", Journal of Immunology, vol 139, pp. 2825–2833.
Embleton et al (1992) "In–cell PCR from mRNA: amplifying and linking the rearranged immunoglobulin heavy and light chain V–genes within single cells", Nucleic Acids Research, vol 20, pp. 3831–3837.
Marks et al (1992) "By–passing immunization: Building high affinity human antibodies by chain shuffling", Bio/Technology, vol 10, pp. 779–783.
Davis et al (1991) "Single chain antibody encoding genes: one–step construction and expression in eucaryotic cells", Bio/Technology, vol 9, pp. 165–169.
George et al (1989) "Prospects for the treatment of B cell tumors using idiotypic vaccination", International Reviews of Immunology, vol 4, pp. 271–310
Tang et al (1992) "Genetic immunication is a simply method for elicting an immune response", Nature, vol 356, pp. 152–1546.
Hinuma et al (1991) "A novel strategy for converting recombinant viral protein into high immunogenic antigen", FEBS Letters, vol 288, pp. 138–142.
Hawkins et al (1992) "Selection of phase antibodies by binding affinity", Journal of Molecular Biology, vol 226, pp. 889–896.
Tao et al (1992) "Idiotype/granulocyte–macrophage colony–stimulating factor fusion protein as a vaccine for B–cell lymphome", Nature, vol 362, pp. 755–758.
Coughlan (1995) "Gene dream fades away", New Scientist, pp. 14–15.

(Continued)

*Primary Examiner*—Anne Marie S. Wehbé
(74) *Attorney, Agent, or Firm*—Morgan Lewis & Bockius LLP

(57) ABSTRACT

The invention relates to a nucleic acid construct for delivery into living cells in vivo for inducing an immune response in a patient to an idiotypic determinant present on a malignant B cell in the patient; the construct directing the expression of a fusion protein, said fusion protein comprising the idiotypic determinant and at least one T helper cell epitope from tetanus toxin. The invention further relates to a method of making the nucleic acid construct, a method of treating a patient, and to a composition comprising the nucleic acid construct.

8 Claims, 19 Drawing Sheets

OTHER PUBLICATIONS

Brown (1995) "Gene therapy oversold by researchers, journalists", The Washington Post, pp. A1 and A22.
Marshall (1995) "Gene therapy's growing pains", Science, vol 269, pp. 1050–1055.
Rosenberg (1995) "Immunotherapy and gene therapy of cancer", Cancer Research, vol 51, pp. 5074s–5079s.
Stevenson et al (1995) "Idiotypic DNA vaccines against B–cell lymphoma" Immunological Reviews, vol 145, pp. 211–228.
Syrengelas et al (1996) "DNA immunization induces protective immunity against B–cell lymphoma" Nature Medicine, vol 2, pp. 1038–1041.

* cited by examiner

I) Vector with Myc Tag

```
                      rbs                M  K  Y  L  L  P  T  A  A
GCATGCAAATTCTATTTCAAGGAGACAGTCATAATGAAATACCTATTGCCTACGGCAGCC
        10        20        30        40        50        60
SphI PelB leader
  A  G  L  L  L  L  A  A  Q  P  A  M  A  Q  V  Q  L  Q  V  D
GCTGGATTGTTATTACTCGCGGCCCAGCCGGCCATGGCCCAGGTGCAGCTGCAGGTCGAC
        70        80        90        100       110       110
                      SfiI                         PstI  SalI Myc Tag (TAG1)
  L  E  I  K  R  A  A  A  E  Q  K  L  I  S  E  E  D  L  N  *
CTCGAGATCAAACGGGCGGCCGCAGAACAAAAACTCATCTCAGAACAGGATCTGAATTAA
        120       130       140       150       160       170
XhoI           NotI

*
TAAGAATTC

ECoRI
```

II) Vector with Histidine Tag (pRH2)

```
                      rbs                M  K  Y  L  L  P  T  A  A
GCATGCAAATTCTATTTCAAGGAGACAGTCATAATGAAATACCTATTGCCTACGGCAGCC
        10        20        30        40        50        60
SphI PelB leader
  A  G  L  L  L  L  A  A  Q  P  A  M  A  Q  V  Q  L  Q  V  G
GCTGGATTGTTATTACTCGCGGCCCAGCCGGCCATGGCCCAGGTCCAGCTGCAGGTCGGC
        70        80         90       100       110       115
                     SfiI  NcoI                     PstI L  E  I  K  R  A  A  A  H  H  H  H  H  H  *  *
CTCGAGATCAAACGGGCGGCCGCACATCACCATCATCACCATTAATAAGAATTC
        120       130       140       150       160
XhoI           NotI                              EcoRI
```

Fig. 2 pVAC1
HindIII
AAG CTT AGC ATG GAC TGG ACC TGG AGG GTC TTC TGC TTG CTG GCT
 K   L   S   M   D   W   T   W   R   V   F   C   L   L   A
        SfiI              <------------VH1 leader------------

GTG GCC CCG GGG GCC CAC TCC CAG GTG CAG CTG CAG GTC GAC CTC
 V   A   P   G   A   H   S   Q   V   Q   L   Q   V   D   L
                         ------------>
                ^ NotI

GAG ATC AAA CGG GCG GCC GCA AGC GCT TGG CGT CAC CCG CAG TTC
 E   I   K   R   A   A   A   S   A   W   R   H   P   Q   F
                                            XbaI

GGT GGT TAA TAA GAA TTG CTC GAG CAT GCA TCT AGA G....
 G   G   *   *

Fig. 5

1 GACGGATCGG GAGATCTCCC GATCCCCTAT GGTCGACTCT CAGTACAATC
51 TGCTCTGATG CCGCATAGTT AAGCCAGTAT CTGCTCCCTG CTTGTGTGTT
101 GGAGGTCGCT GAGTAGTGCG CGAGCAAAAT TTAAGCTACA ACAAGGCAAG
151 GCTTGACCGA CAATTGCATG AAGAATCTGC TTAGGGTTAG GCGTTTTGCG
201 CTGCTTCGCG ATGTACGGGC CAGATATACG CGTATCTGAG GGGACTAGGG
251 TGTGTTTAGG CGAAAAGCGG GGCTTCGGTT GTACGCGGTT AGGAGTCCCC
301 TCAGGATATA GTAGTTTCGC TTTTGCATAG GGAGGGGGAA ATGTAGTCTT
351 ATGCAATACA CTTGTAGTCT TGCAACATGG TAACGATGAG TTAGCAACAT
401 GCCTTACAAG GAGAGAAAAA GCACCGTGCA TGCCGATTGG TGGAAGTAAG
451 GTGGTACGAT CGTGCCTTAT TAGGAAGGCA ACAGACAGGT CTGACATGGA
501 TTGGACGAAC CACTGAATTC CGCATTGCAG AGATAATTGT ATTTAAGTGC
551 CTAGCTCGAT ACAATAAACG CCATTTGACC ATTCACCACA TTGGTGTGCA
601 CCTCCaagct tagcatggac tggacctgga gggtcttctg cttgctggct
651 gtggccccgg gggcccactc ccaggtgcag ctgcaggtcg acctcgagat
701 caaacgggcg gccgcaagcg cttggcgtca cccgcagttc ggtggttaat
751 aagaattggc cgctcGAGCA TGCATCTAGA GCTCGCTGAT CAGCCTCGAC
801 TGTGCCTTCT AGTTGCCAGC CATCTGTTGT TTGCCCCTCC CCCGTGCCTT
851 CCTTGACCCT GGAAGGTGCC ACTCCCACTG TCCTTTCCTA ATAAAATGAG
901 GAAATTGCAT CGCATTGTCT GAGTAGGTGT CATTCTATTC TGGGGGGTGG
951 GGTGGGGCAG GACAGCAAGG GGGAGGATTG GGAAGACAAT AGCAGGCATG
1001 CTGGGGATGC GGTGGGCTCT ATGGAACCAG CTGGGGCTCG AGGGGGGATC
1051 CCCACGCGCC CTGTAGCGGC GCATTAAGCG CGGCGGGTGT GGTGGTTACG
1101 CGCAGCGTGA CCGCTACACT TGCCAGCGCC CTAGCGCCCG CTCCTTTCGC
1151 TTTCTTCCCT TCCTTTCTCG CCACGTTCGC CGGCTTTCCC CGTCAAGCTC
1201 TAAATCGGGG CATCCCTTTA GGGTTCCGAT TTAGTGCTTT ACGGCACCTC
1251 GACCCCAAAA AACTTGATTA GGGTGATGGT TCACGTAGTG GGCCATCGCC
1301 CTGATAGACG GTTTTTCGCC CTTTGACGTT GGAGTCCACG TTCTTTAATA
1351 GTGGACTCTT GTTCCAAACT GGAACAACAC TCAACCCTAT CTCGGTCTAT

Fig. 7 (i)

1401 TCTTTTGATT TATAAGGGAT TTTGGGGATT TCGGCCTATT GGTTAAAAAA
1451 TGAGCTGATT TAACAAAAAT TTAACGCGAA TTTTAACAAA ATATTAACGT
1501 TTACAATTTA AATATTTGCT TATACAATCT TCCTGTTTTT GGGGCTTTTC
1551 TGATTATCAA CCGGGGTGGG TACCGAGCTC GAATTCTGTG GAATGTGTGT
1601 CAGTTAGGGT GTGGAAAGTC CCCAGGCTCC CCAGGCAGGC AGAAGTATGC
1651 AAAGCATGCA TCTCAATTAG TCAGCAACCA GGTGTGGAAA GTCCCCAGGC
1701 TCCCCAGCAG GCAGAAGTAT GCAAAGCATG CATCTCAATT AGTCAGCAAC
1751 CATAGTCCCG CCCCTAACTC CGCCCATCCC GCCCCTAACT CCGCCCAGTT
1801 CCGCCCATTC TCCGCCCCAT GGCTGACTAA TTTTTTTTAT TTATGCAGAG
1851 GCCGAGGCCG CGAAATGACC GACCAAGCGA CGCCCAACCT GCCATCACGA
1901 GATTTCGATT CCACCGCCGC CTTCTATGAA AGGTTGGCCT TCGGAATCGT
1951 TTTCCGGGAC GCCGGCTGGA TGATCCTCCA GCGCGGGGAT CTCATGCTGG
2001 AGTTCTTCGC CCACCCCAAC TTGTTTATTG CAGCTTATAA TGGTTACAAA
2051 TAAAGCAATA GCATCACAAA TTTCACAAAT AAAGCATTTT TTTCACTGCA
2101 TTCTAGTTGT GGTTTGTCCA AACTCATCAA TGTATCTTAT CATGTCTGGA
2151 TCCCGTCGAC CTCGAGAGCT TGGCGTAATC ATGGTCATAG CTGTTTCCTG
2201 TGTGAAATTG TTATCCGCTC ACAATTCCAC ACAACATACG AGCCGGAAGC
2251 ATAAAGTGTA AAGCCTGGGG TGCCTAATGA GTGAGCTAAC TCACATTAAT
2301 TGCGTTGCGC TCACTGCCCG CTTTCCAGTC GGGAAACCTG TCGTGCCAGC
2351 TGCATTAATG AATCGGCCAA CGCGCGGGGA GAGGCGGTTT GCGTATTGGG
2401 CGCTCTTCCG CTTCCTCGCT CACTGACTCG CTGCGCTCGG TCGTTCGGCT
2451 GCGGCGAGCG GTATCAGCTC ACTCAAAGGC GGTAATACGG TTATCCACAG
2501 AATCAGGGGA TAACGCAGGA AAGAACATGT GAGCAAAAGG CCAGCAAAAG
2551 GCCAGGAACC GTAAAAAGGC CGCGTTGCTG GCGTTTTTCC ATAGGCTCCG
2601 CCCCCCTGAC GAGCATCACA AAAATCGACG CTCAAGTCAG AGGTGGCGAA
2651 ACCCGACAGG ACTATAAAGA TACCAGGCGT TTCCCCCTGG AAGCTCCCTC
2701 GTGCGCTCTC CTGTTCCGAC CCTGCCGCTT ACCGGATACC TGTCCGCCTT
2751 TCTCCCTTCG GGAAGCGTGG CGCTTTCTCA ATGCTCACGC TGTAGGTATC
2801 TCAGTTCGGT GTAGGTCGTT CGCTCCAAGC TGGGCTGTGT GCACGAACCC
2851 CCCGTTCAGC CCGACCGCTG CGCCTTATCC GGTAACTATC GTCTTGAGTC
2901 CAACCCGGTA AGACACGACT TATCGCCACT GGCAGCAGCC ACTGGTAACA
2951 GGATTAGCAG AGCGAGGTAT GTAGGCGGTG CTACAGAGTT CTTGAAGTGG
3001 TGGCCTAACT ACGGCTACAC TAGAAGGACA GTATTTGGTA TCTGCGCTCT

Fig. 7 (ii)

3051 GCTGAAGCCA GTTACCTTCG GAAAAAGAGT TGGTAGCTCT TGATCCGGCA
3101 AACAAACCAC CGCTGGTAGC GGTGGTTTTT TTGTTTGCAA CCAGCAGATT
3151 ACGCGCAGAA AAAAAGGATC TCAAGAAGAT CCTTTGATCT TTTCTACGGG
3201 GTCTGACGCT CAGTGGAACG AAAACTCACG TTAAGGGATT TTGGTCATGA
3251 GATTATCAAA AAGGATCTTC ACCTAGATCC TTTTAAATTA AAAATGAAGT
3301 TTTAAATCAA TCTAAAGTAT ATATGAGTAA ACTTGGTCTG ACAGTTACCA
3351 ATGCTTAATC AGTGAGGCAC CTATCTCAGC GATCTGTCTA TTTCGTTCAT
3401 CCATAGTTGC CTGACTCCCC GTCGTGTAGA TAACTACGAT ACGGGAGGGC
3451 TTACCATCTG GCCCCAGTGC TGCAATGATA CCGCGAGACC CACGCTCACC
3501 GGCTCCAGAT TTATCAGCAA TAAACCAGCC AGCCGGAAGG GCCGAGCGCA
3551 GAAGTGGTCC TGCAACTTTA TCCGCCTCCA TCCAGTCTAT TAATTGTTGC
3601 CGGGAAGCTA GAGTAAGTAG TTCGCCAGTT AATAGTTTGC GCAACGTTGT
3651 TGCCATTGCT ACAGGCATCG TGGTGTCACG CTCGTCGTTT GGTATGGCTT
3701 CATTCAGCTC CGGTTCCCAA CGATCAAGGC GAGTTACATG ATCCCCCATG
3751 TTGTGCAAAA AAGCGGTTAG CTCCTTCGGT CCTCCGATCG TTGTCAGAAG
3801 TAAGTTGGCC GCAGTGTTAT CACTCATGGT TATGGCAGCA CTGCATAATT
3851 CTCTTACTGT CATGCCATCC GTAAGATGCT TTTCTGTGAC TGGTGAGTAC
3901 TCAACCAAGT CATTCTGAGA ATAGTGTATG CGGCGACCGA GTTGCTCTTG
3951 CCCGGCGTCA ATACGGGATA ATACCGCGCC ACATAGCAGA ACTTTAAAAG
4001 TGCTCATCAT TGGAAAACGT TCTTCGGGGC GAAAACTCTC AAGGATCTTA
4051 CCGCTGTTGA GATCCAGTTC GATGTAACCC ACTCGTGCAC CCAACTGATC
4101 TTCAGCATCT TTTACTTTCA CCAGCGTTTC TGGGTGAGCA AAAACAGGAA
4151 GGCAAAATGC CGCAAAAAAG GGAATAAGGG CGACACGGAA ATGTTGAATA
4201 CTCATACTCT TCCTTTTTCA ATATTATTGA AGCATTTATC AGGGTTATTG
4251 TCTCATGAGC GGATACATAT TTGAATGTAT TTAGAAAAAT AAACAAATAG
4301 GGGTTCCGCG CACATTTCCC CGAAAAGTGC CACCTGACGT C

Fig. 7 (iii)

Serum samples pre and post Immunisation

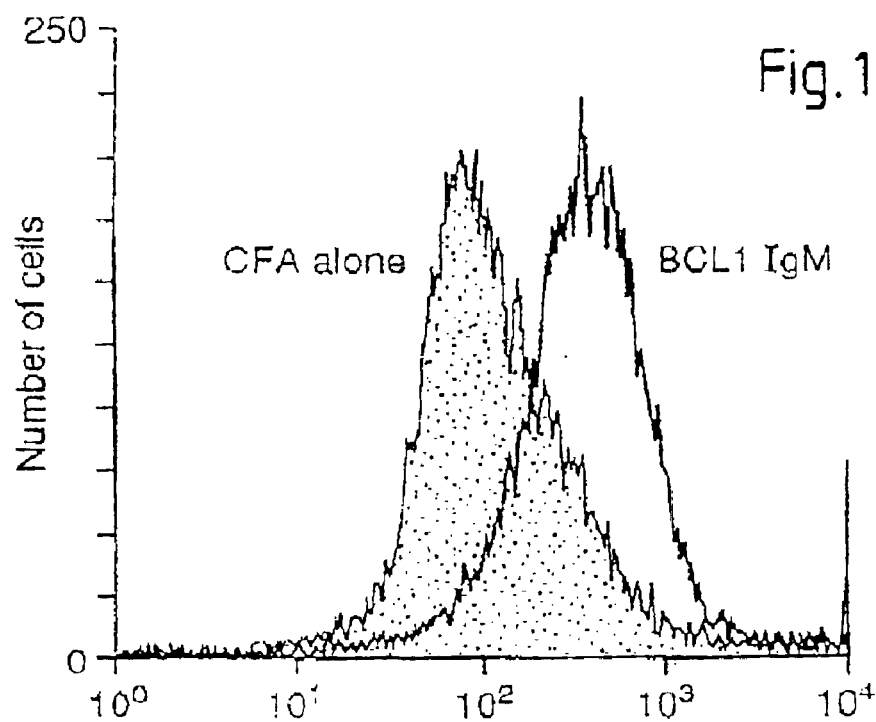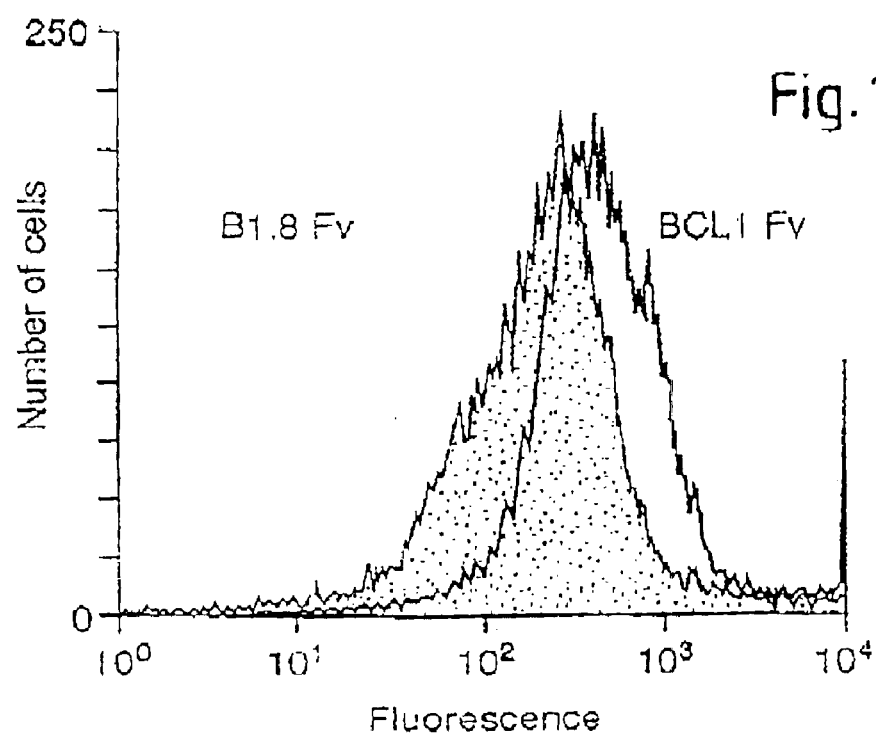

SEQUENCE LISTING (1) GENERAL INFORMATION:

(iii) NUMBER OF SEQUENCES: 79

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

CAGGTGCAGC TGGTGCAGTC TG                 22

(2) INFORMATION FOR SEQ ID NO:2:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

CAGGTCAACT TAAGGGAGTC TG                                    22

(2) INFORMATION FOR SEQ ID NO:3:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

GAGGTGCAGC TGGTGGAGTC TG                                    22

(2) INFORMATION FOR SEQ ID NO:4:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

CAGGTGCAGC TGCAGGAGTC GG                                    22

(2) INFORMATION FOR SEQ ID NO:5:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

GAGGTGCAGC TGCTGCAGTC TG                                    22

(2) INFORMATION FOR SEQ ID NO:6:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

CAGGTACAGC TGCAGCAGTC AG                                            22

(2) INFORMATION FOR SEQ ID NO:7:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

TGAGGAGACG GTGACCAGGG TGCC                                          24

(2) INFORMATION FOR SEQ ID NO:8:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

TGAGGAGACG GTGACCAGGG TTCC                                          24

(2) INFORMATION FOR SEQ ID NO:9:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

TGAAGAGACG GTGACCATTG TCCC                                          24

(2) INFORMATION FOR SEQ ID NO:10:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

TGAGGAGACG GTGACCGTGG TCCC                                          24

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

GACATCCAGA TGACCCAGTC TCC                                          23

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

GATATTGTGA TGACTCAGTC TCC                                          23

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

GAAATTGTGT TGACGCAGTC TCC                                          23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

GAAACGACAC TCACGCAGTC TCC                                          23

(2) INFORMATION FOR SEQ ID NO:15:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

ACGTTTGATC TCCACCTTGG TCCC                                    24

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

ACGTTTGATA TCCACTTTGG TCCC                                    24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

ACGTTTAATC TCCAGTCGTG TCCC                                    24

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

CAGTCTGTGT TGACGCAGCC GCCCTC                                  26

(2) INFORMATION FOR SEQ ID NO:19:

(i) SEQUENCE CHARACTERISTICS:
        (A) LENGTH: 26 base pairs

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

CAGTCTGCCC TGACTCAGCC TGCCTC                                    26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

TCCTATGAGC TGACTCAGCC ACVCTC                                    26

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

CACGTTATAC TGACTCAACC GCCCTC                                    26

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

ACCTAGGACG GTGACCTTGG TCCC                                      24

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO:23:

ACCTAGGACG GTCAGCTTGG TCCC                                                  24

(2) INFORMATION FOR SEQ ID NO:24:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

ACCGAGGACG GTCAGCTGGG TGCC                                                  24

(2) INFORMATION FOR SEQ ID NO:25:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

TCGCGGCCCA ACCGGCCATG GCCCAGGTGC AGCTGGTGCA G                                41

(2) INFORMATION FOR SEQ ID NO:26:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

TCGCGGCCCA ACCGGCCATG GCCCAGGTCA ACTTAAGGGA G                                41

(2) INFORMATION FOR SEQ ID NO:27:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

-continued (iii) HYPOTHETICAL: NO (iv) ANTI-SENSE: NO (xi) SEQUENCE DESCRIPTION: SEQ ID NO:27:

TCGCGGCCCA ACCGGCCATG GCCGAGGTGC AGCTGGTGGA G     41

(2) INFORMATION FOR SEQ ID NO:28:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

TCGCGGCCCA ACCGGCCATG GCCCAGGTGC AGCTGCAGGA G     41

(2) INFORMATION FOR SEQ ID NO:29:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:29:

TCGCGGCCCA ACCGGCCATG GCCGAGGTGC AGCTGCTGCA G     41

(2) INFORMATION FOR SEQ ID NO:30:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:30:

TCGCGGCCCA ACCGGCCATG GCCCAGGTAC AGCTGCAGCA G     41

(2) INFORMATION FOR SEQ ID NO:31:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:31:

AGAGCCACCT CCGCCTGAAC CGCCTCCACC TGAGGAGACG GTGACCAGGG    50

(2) INFORMATION FOR SEQ ID NO:32:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:32:

AGAGCCACCT CCGCCTGAAC CGCCTCCACC TGAGGAGACG GTGACCAGGG    50

(2) INFORMATION FOR SEQ ID NO:33:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

AGAGCCACCT CCGCCTGAAC CGCCTCCACC TGAAGAGACG GTGACCATTG    50

(2) INFORMATION FOR SEQ ID NO:34:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

AGAGCCACCT CCGCCTGAAC CGCCTCCACC TGAGGAGACG GTGACCGTGG    50

(2) INFORMATION FOR SEQ ID NO:35:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:35:

```
GGCGGAGGTG GCTCTGGCGG TGGCGGATCG GACATCCAGA TGACCCAG                48
```

(2) INFORMATION FOR SEQ ID NO:36:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

```
GGCGGAGGTG GCTCTGGCGG TGGCGGATCG GATATTGTGA TGACTCAGT             49
```

(2) INFORMATION FOR SEQ ID NO:37:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

```
GGCGGAGGTG GCTCTGGCGG TGGCGGATCG GAAATTGTGT TGACGCAGT             49
```

(2) INFORMATION FOR SEQ ID NO:38:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:38:

```
GGCGGAGGTG GCTCTGGCGG TGGCGGATCG GAAACGACAC TCACGCAG              48
```

(2) INFORMATION FOR SEQ ID NO:39:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:39:

```
GATATGAGAT ACTGCGGCCG CACGTTTGAT CTCCACCTTG G                     41
```

(2) INFORMATION FOR SEQ ID NO:40:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:40:

```
GATATGAGAT ACTGCGGCCG CACGTTTGAT ATCCACTTTG G                    41
```

(2) INFORMATION FOR SEQ ID NO:41:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:41:

```
GATATGAGAT ACTGCGGCCG CACGTTTAAT CTCCAGTCGT G                    41
```

(2) INFORMATION FOR SEQ ID NO:42:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:42:

```
GGCGGAGGTG GCTCTGGCGG TGGCGGATCG CAGTCTGTGT TGACGCAG             48
```

(2) INFORMATION FOR SEQ ID NO:43:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:43:

```
GGCGGAGGTG GCTCTGGCGG TGGCGGATCG CAGTCTGCCC TGACTCAG             48
```

(2) INFORMATION FOR SEQ ID NO:44:

(i) SEQUENCE CHARACTERISTICS:

```
            (A) LENGTH: 48 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:44:

GGCGGAGGTG GCTCTGGCGG TGGCGGATCG TCCTATGAGC TGACTCAG              48

(2) INFORMATION FOR SEQ ID NO:45:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:45:

GGCGGAGGTG GCTCTGGCGG TGGCGGATCG CACGTTATAC TGACTCAAC             49

(2) INFORMATION FOR SEQ ID NO:46:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

GATATGAGAT ACTGCGGCCG CACCTAGGAC GGTGACCTTG G                     41

(2) INFORMATION FOR SEQ ID NO:47:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:47:

GATATGAGAT ACTGCGGCCG CACCTAGGAC GGTCAGCTTG G                     41

(2) INFORMATION FOR SEQ ID NO:48:

(i) SEQUENCE CHARACTERISTICS:
            (A) LENGTH: 41 base pairs
            (B) TYPE: nucleic acid
            (C) STRANDEDNESS: single
```

(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:48:

GATATGAGAT ACTGCGGCCG CACCGAGGAC GGTCAGCTGG G                    41

(2) INFORMATION FOR SEQ ID NO:49:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:49:

CTGCAGGAGC TCGAGATCAA ACGGGCGGCC GCACCTCATC AAGTCTATAA TATC      54

(2) INFORMATION FOR SEQ ID NO:50:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:50:

GCCAGAACGG GGTTTGGCC                                              19

(2) INFORMATION FOR SEQ ID NO:51:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:51:

TTTGATCTCG AGCTCCTGCA GGGCCGGCTG GGCCGCACTG AGCCGGGCG AAGCAGT     57

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:52:

AATTACATTG TGCATACAGA CCC                                              23

(2) INFORMATION FOR SEQ ID NO:53:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:53:

TAATCACTAC AGATCTAGAC TGACATGGCG CGT                                   33

(2) INFORMATION FOR SEQ ID NO:54:

(i) SEQUENCE CHARACTERISTICS:
          (A) LENGTH: 46 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:54:

TACTCGCGGC CCAACCGGCC ATGGCCCAGG TSMARCTGCA GSAGTC                     46

(2) INFORMATION FOR SEQ ID NO:55:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:55:

AACAGTTTCT GCGGCCGCCT CCTCAGAGGA C                                     31

(2) INFORMATION FOR SEQ ID NO:56:

(i) SEQUENCE CHARACTERISTICS:
          (A) LENGTH: 172 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:56:

AAGCTTAGCA TGGACTGGAC CTGGAGGGTC TTCTGCTTGC TGGCTGTGGC CCCGGGGGCC        60

CACTCCCAGG TGCAGCTGCA GGTCGACCTC GAGATCAAAC GGGCGGCCGC AAGCGCTTGG       120

CGTCACCCGC AGTTCGGTGG TTAATAAGAA TTGCTCGAGC ATGCATCTAG AG              172

(2) INFORMATION FOR SEQ ID NO:57:

(i) SEQUENCE CHARACTERISTICS:
         (A) LENGTH: 47 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:57:

Lys Leu Ser Met Asp Trp Thr Trp Arg Val Phe Cys Leu Leu Ala Val
1               5                  10                  15

Ala Pro Gly Ala His Ser Gln Val Gln Leu Gln Val Asp Leu Glu Ile
            20                  25                  30

Lys Arg Ala Ala Ala Ser Ala Trp Arg His Pro Gln Phe Gly Gly
        35                  40                  45

(2) INFORMATION FOR SEQ ID NO:58:

(i) SEQUENCE CHARACTERISTICS:
         (A) LENGTH: 4341 base pairs
         (B) TYPE: nucleic acid
         (C) STRANDEDNESS: single
         (D) TOPOLOGY: circular (ii) MOLECULE TYPE: DNA (genomic)

(iii) HYPOTHETICAL: NO (iv) ANTI-SENSE: NO (xi) SEQUENCE DESCRIPTION: SEQ ID NO:58:

GACGGATCGG GAGATCTCCC GATCCCCTAT GGTCGACTCT CAGTACAATC TGCTCTGATG        60

CCGCATAGTT AAGCCAGTAT CTGCTCCCTG CTTGTGTGTT GGAGGTCGCT GAGTAGTGCG       120

CGAGCAAAAT TTAAGCTACA ACAAGGCAAG CTTGACCGA CAATTGCATG AAGAATCTGC        180

TTAGGGTTAG GCGTTTTGCG CTGCTTCGCG ATGTACGGGC CAGATATACG CGTATCTGAG       240

GGGACTAGGG TGTGTTTAGG CGAAAAGCGG GGCTTCGGTT GTACGCGGTT AGGAGTCCCC       300

TCAGGATATA GTAGTTTCGC TTTTGCATAG GGAGGGGGAA ATGTAGTCTT ATGCAATACA       360

CTTGTAGTCT TGCAACATGG TAACGATGAG TTAGCAACAT GCCTTACAAG GAGAGAAAAA      420

GCACCGTGCA TGCCGATTGG TGGAAGTAAG GTGGTACGAT CGTGCCTTAT TAGGAAGGCA      480

ACAGACAGGT CTGACATGGA TTGGACGAAC CACTGAATTC CGCATTGCAG AGATAATTGT       540

ATTTAAGTGC CTAGCTCGAT ACAATAAACG CCATTTGACC ATTCACCACA TTGGTGTGCA       600

CCTCCAAGCT TAGCATGGAC TGGACCTGGA GGGTCTTCTG CTTGCTGGCT GTGGCCCCGG       660

GGGCCCACTC CCAGGTGCAG CTGCAGGTCG ACCTCGAGAT CAAACGGGCG GCCGCAAGCG       720

```
CTTGGCGTCA CCCGCAGTTC GGTGGTTAAT AAGAATTGGC CGCTCGAGCA TGCATCTAGA    780

GCTCGCTGAT CAGCCTCGAC TGTGCCTTCT AGTTGCCAGC CATCTGTTGT TTGCCCCTCC    840

CCCGTGCCTT CCTTGACCCT GGAAGGTGCC ACTCCCACTG TCCTTTCCTA ATAAAATGAG    900

GAAATTGCAT CGCATTGTCT GAGTAGGTGT CATTCTATTC TGGGGGGTGG GGTGGGGCAG    960

GACAGCAAGG GGGAGGATTG GGAAGACAAT AGCAGGCATG CTGGGGATGC GGTGGGCTCT   1020

ATGGAACCAG CTGGGGCTCG AGGGGGGATC CCCACGCGCC CTGTAGCGGC GCATTAAGCG   1080

CGGCGGGTGT GGTGGTTACG CGCAGCGTGA CCGCTACACT TGCCAGCGCC CTAGCGCCCG   1140

CTCCTTTCGC TTTCTTCCCT TCCTTTCTCG CCACGTTCGC CGGCTTTCCC CGTCAAGCTC   1200

TAAATCGGGG CATCCCTTTA GGGTTCCGAT TTAGTGCTTT ACGGCACCTC GACCCCAAAA   1260

AACTTGATTA GGGTGATGGT TCACGTAGTG GGCCATCGCC CTGATAGACG GTTTTTCGCC   1320

CTTTGACGTT GGAGTCCACG TTCTTTAATA GTGGACTCTT GTTCCAAACT GGAACAACAC   1380

TCAACCCTAT CTCGGTCTAT TCTTTTGATT TATAAGGGAT TTTGGGGATT TCGGCCTATT   1440

GGTTAAAAAA TGAGCTGATT TAACAAAAAT TTAACGCGAA TTTTAACAAA ATATTAACGT   1500

TTACAATTTA AATATTTGCT TATACAATCT TCCTGTTTTT GGGGCTTTTC TGATTATCAA   1560

CCGGGGTGGG TACCGAGCTC GAATTCTGTG GAATGTGTGT CAGTTAGGGT GTGGAAAGTC   1620

CCCAGGCTCC CCAGGCAGGC AGAAGTATGC AAAGCATGCA TCTCAATTAG TCAGCAACCA   1680

GGTGTGGAAA GTCCCCAGGC TCCCCAGCAG GCAGAAGTAT GCAAAGCATG CATCTCAATT   1740

AGTCAGCAAC CATAGTCCCG CCCCTAACTC CGCCCATCCC GCCCCTAACT CCGCCCAGTT   1800

CCGCCCATTC TCCGCCCCAT GGCTGACTAA TTTTTTTTAT TTATGCAGAG GCCGAGGCCG   1860

CGAAATGACC GACCAAGCGA CGCCCAACCT GCCATCACGA GATTTCGATT CCACCGCCGC   1920

CTTCTATGAA AGGTTGGGCT TCGGAATCGT TTTCCGGGAC GCCGGCTGGA TGATCCTCCA   1980

GCGCGGGGAT CTCATGCTGG AGTTCTTCGC CCACCCCAAC TTGTTTATTG CAGCTTATAA   2040

TGGTTACAAA TAAAGCAATA GCATCACAAA TTTCACAAAT AAAGCATTTT TTTCACTGCA   2100

TTCTAGTTGT GGTTTGTCCA AACTCATCAA TGTATCTTAT CATGTCTGGA TCCCGTCGAC   2160

CTCGAGAGCT TGGCGTAATC ATGGTCATAG CTGTTTCCTG TGTGAAATTG TTATCCGCTC   2220

ACAATTCCAC ACAACATACG AGCCGGAAGC ATAAAGTGTA AAGCCTGGGG TGCCTAATGA   2280

GTGAGCTAAC TCACATTAAT TGCGTTGCGC TCACTGCCCG CTTTCCAGTC GGGAAACCTG   2340

TCGTGCCAGC TGCATTAATG AATCGGCCAA CGCGCGGGGA GAGGCGGTTT GCGTATTGGG   2400

CGCTCTTCCG CTTCCTCGCT CACTGACTCG CTGCGCTCGG TCGTTCGGCT GCGGCGAGCG   2460

GTATCAGCTC ACTCAAAGGC GGTAATACGG TTATCCACAG AATCAGGGGA TAACGCAGGA   2520

AAGAACATGT GAGCAAAAGG CCAGCAAAAG GCCAGGAACC GTAAAAAGGC CGCGTTGCTG   2580

GCGTTTTTCC ATAGGCTCCG CCCCCCTGAC GAGCATCACA AAAATCGACG CTCAAGTCAG   2640

AGGTGGCGAA ACCCGACAGG ACTATAAAGA TACCAGGCGT TTCCCCCTGG AAGCTCCCTC   2700

GTGCGCTCTC CTGTTCCGAC CCTGCCGCTT ACCGGATACC TGTCCGCCTT TCTCCCTTCG   2760

GGAAGCGTGG CGCTTTCTCA ATGCTCACGC TGTAGGTATC TCAGTTCGGT GTAGGTCGTT   2820

CGCTCCAAGC TGGGCTGTGT GCACGAACCC CCCGTTCAGC CCGACCGCTG CGCCTTATCC   2880

GGTAACTATC GTCTTGAGTC AACCCGGTA AGACACGACT TATCGCCACT GGCAGCAGCC   2940

ACTGGTAACA GGATTAGCAG AGCGAGGTAT GTAGGCGGTG CTACAGAGTT CTTGAAGTGG   3000

TGGCCTAACT ACGGCTACAC TAGAAGGACA GTATTTGGTA TCTGCGCTCT GCTGAAGCCA   3060

GTTACCTTCG GAAAAAGAGT TGGTAGCTCT TGATCCGGCA ACAAACCAC CGCTGGTAGC    3120
```

```
GGTGGTTTTT TTGTTTGCAA GCAGCAGATT ACGCGCAGAA AAAAAGGATC TCAAGAAGAT    3180

CCTTTGATCT TTTCTACGGG GTCTGACGCT CAGTGGAACG AAAACTCACG TTAAGGGATT    3240

TTGGTCATGA GATTATCAAA AAGGATCTTC ACCTAGATCC TTTTAAATTA AAAATGAAGT    3300

TTTAAATCAA TCTAAAGTAT ATATGAGTAA ACTTGGTCTG ACAGTTACCA ATGCTTAATC    3360

AGTGAGGCAC CTATCTCAGC GATCTGTCTA TTTCGTTCAT CCATAGTTGC CTGACTCCCC    3420

GTCGTGTAGA TAACTACGAT ACGGGAGGGC TTACCATCTG GCCCCAGTGC TGCAATGATA    3480

CCGCGAGACC CACGCTCACC GGCTCCAGAT TTATCAGCAA TAAACCAGCC AGCCGGAAGG    3540

GCCGAGCGCA GAAGTGGTCC TGCAACTTTA TCCGCCTCCA TCCAGTCTAT TAATTGTTGC    3600

CGGGAAGCTA GAGTAAGTAG TTCGCCAGTT AATAGTTTGC GCAACGTTGT TGCCATTGCT    3660

ACAGGCATCG TGGTGTCACG CTCGTCGTTT GGTATGGCTT CATTCAGCTC CGGTTCCCAA    3720

CGATCAAGGC GAGTTACATG ATCCCCCATG TTGTGCAAAA AAGCGGTTAG CTCCTTCGGT    3780

CCTCCGATCG TTGTCAGAAG TAAGTTGGCC GCAGTGTTAT CACTCATGGT TATGGCAGCA    3840

CTGCATAATT CTCTTACTGT CATGCCATCC GTAAGATGCT TTTCTGTGAC TGGTGAGTAC    3900

TCAACCAAGT CATTCTGAGA ATAGTGTATG CGGCGACCGA GTTGCTCTTG CCCGGCGTCA    3960

ATACGGGATA ATACCGCGCC ACATAGCAGA ACTTTAAAAG TGCTCATCAT TGGAAAACGT    4020

TCTTCGGGGC GAAAACTCTC AAGGATCTTA CCGCTGTTGA GATCCAGTTC GATGTAACCC    4080

ACTCGTGCAC CCAACTGATC TTCAGCATCT TTTACTTTCA CCAGCGTTTC TGGGTGAGCA    4140

AAAACAGGAA GGCAAAATGC CGCAAAAAAG GGAATAAGGG CGACACGGAA ATGTTGAATA    4200

CTCATACTCT TCCTTTTTCA ATATTATTGA AGCATTTATC AGGGTTATTG TCTCATGAGC    4260

GGATACATAT TTGAATGTAT TTAGAAAAAT AAACAAATAG GGGTTCCGCG CACATTTCCC    4320

CGAAAAGTGC CACCTGACGT C                                              4341

(2) INFORMATION FOR SEQ ID NO:59:

(i) SEQUENCE CHARACTERISTICS:
        (A) LENGTH: 189 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:59:

GCATGCAAAT TCTATTTCAA GGAGACAGTC ATAATGAAAT ACCTATTGCC TACGGCAGCC     60

GCTGGATTGT TATTACTCGC GGCCCAGCCG GCCATGGCCC AGGTGCAGCT GCAGGTCGAC    120

CTCGAGATCA AACGGGCGGC CGCAGAACAA AAACTCATCT CAGAAGAGGA TCTGAATTAA    180

TAAGAATTC                                                            189

(2) INFORMATION FOR SEQ ID NO:60:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide
```

(iii) HYPOTHETICAL: NO (iv) ANTI-SENSE: NO (v) FRAGMENT TYPE: internal (xi) SEQUENCE DESCRIPTION: SEQ ID NO:60:

Met Lys Tyr Leu Leu Pro Thr Ala Ala Ala Gly Leu Leu Leu Ala
1               5                   10                  15

Ala Gln Pro Ala Met Ala Gln Val Gln Leu Gln Val Asp Leu Glu Ile
            20                  25                  30

Lys Arg Ala Ala Ala Glu Gln Lys Leu Ile Ser Glu Glu Asp Leu Asn
        35                  40                  45

(2) INFORMATION FOR SEQ ID NO:61:

(i) SEQUENCE CHARACTERISTICS:
        (A) LENGTH: 174 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:61:

GCATGCAAAT TCTATTTCAA GGAGACAGTC ATAATGAAAT ACCTATTGCC TACGGCAGCC      60

GCTGGATTGT TATTACTCGC GGCCCAGCCG GCCATGGCCC AGGTGCAGCT GCAGGTCGGC     120

CTCGAGATCA AACGGGCGGC CGCACATCAC CATCATCACC ATTAATAAGA ATTC          174

(2) INFORMATION FOR SEQ ID NO:62:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:62:

Met Lys Tyr Leu Leu Pro Thr Ala Ala Ala Gly Leu Leu Leu Ala
1               5                   10                  15

Ala Gln Pro Ala Met Ala Gln Val Gln Leu Gln Val Gly Leu Glu Ile
            20                  25                  30

Lys Arg Ala Ala Ala His His His His His
        35                  40

(2) INFORMATION FOR SEQ ID NO:63:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

-continued (iii) HYPOTHETICAL: NO (iv) ANTI-SENSE: NO (xi) SEQUENCE DESCRIPTION: SEQ ID NO:63:

ACTGCTTCGC CCGGCTCCAG TGCGGCCCAG CCGGCCATGG CCCAGGTGCA GCTGCAG    57

(2) INFORMATION FOR SEQ ID NO:64:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:64:

Thr Ala Ser Pro Gly Ser Ser Ala Ala Gln Pro Ala Met Ala Gln Val
1               5                   10                  15

Gln Leu Gln (2) INFORMATION FOR SEQ ID NO:65:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:65:

GTCCTCGAGG AGGCGGCCGC ACCTCATCAA GTCTAT    36

(2) INFORMATION FOR SEQ ID NO:66:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:66:

Val Leu Glu Glu Ala Ala Ala Pro His Gln Val Tyr
1               5                   10

(2) INFORMATION FOR SEQ ID NO:67:

(i) SEQUENCE CHARACTERISTICS:
        (A) LENGTH: 41 base pairs
        (B) TYPE: nucleic acid

```
        (C) STRANDEDNESS: single
        (D) TOPOLOGY: linear (xi) SEQUENCE DESCRIPTION: SEQ ID NO:67:

TCGCGGCCCA ACCGGCCATG GCCCAGGTGC AGCTGCAGGA G                          41

(2) INFORMATION FOR SEQ ID NO:68:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:68:

TCGCGGCCCA ACCGGCCATG GCCCAGGTGC AGCTACAGCA G                          41

(2) INFORMATION FOR SEQ ID NO:69:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:69:

TTTCATAGGT CCGGGTCCAC CTAGGACGGT GACCTT                                36

(2) INFORMATION FOR SEQ ID NO:70:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:70:

TTTCATAGGT CCGGGTCCAC CTAGGACGGT CAGCTT                                36

(2) INFORMATION FOR SEQ ID NO:71:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:71:

TTTCATAGGT CCGGGTCCTC GTTTGATCTC CACCTT                                36

(2) INFORMATION FOR SEQ ID NO:72:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:72:

GGACCCGGAC CTATGAAAAA CCTTGATTGT TG                                    32

(2) INFORMATION FOR SEQ ID NO:73:

(i) SEQUENCE CHARACTERISTICS:
        (A) LENGTH: 33 base pairs
        (B) TYPE: nucleic acid
        (C) STRANDEDNESS: single
```

(D) TOPOLOGY: linear (xi) SEQUENCE DESCRIPTION: SEQ ID NO:73:

TAATGCGGCC GCTTAGTCGT TGGTCCAACC TTC                33

(2) INFORMATION FOR SEQ ID NO:74:

(i) SEQUENCE CHARACTERISTICS:
        (A) LENGTH: 98 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:74:

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys (2) INFORMATION FOR SEQ ID NO:75:

(i) SEQUENCE CHARACTERISTICS:
        (A) LENGTH: 98 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:75:

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys (2) INFORMATION FOR SEQ ID NO:76:

(i) SEQUENCE CHARACTERISTICS:
        (A) LENGTH: 97 amino acids
        (B) TYPE: amino acid
        (C) STRANDEDNESS:

(D) TOPOLOGY: linear (ii) MOLECULE TYPE: peptide (xi) SEQUENCE DESCRIPTION: SEQ ID NO:76:

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```

(2) INFORMATION FOR SEQ ID NO:77:

(i) SEQUENCE CHARACTERISTICS:
        (A) LENGTH: 95 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:77:

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp
                85                  90                  95
```

(2) INFORMATION FOR SEQ ID NO:78:

(i) SEQUENCE CHARACTERISTICS:
        (A) LENGTH: 98 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:78:

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

-continued

```
Met Ile Tyr Glu Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65              70                  75                  80

Gln Ala Glu Asp Glu Ala Asp Tyr Tyr Cys Ser Ser Tyr Thr Ser Ser
                 85                  90                  95

Ser Thr (2) INFORMATION FOR SEQ ID NO:79:

(i) SEQUENCE CHARACTERISTICS:
        (A) LENGTH: 96 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:79:

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65              70                  75                  80

Pro Glu Asp Phe Ala Val Tyr Tyr Cys Gln Gln Tyr Gly Ser Ser Pro
                 85                  90                  95
```

IMMUNE RESPONSES TO FUSION PROTEINS

This is a continuation-in-part of application Ser. No. 08/411,622, filed 14 Jun. 1995 now abandoned.

FIELD OF THE INVENTION

This invention relates to a method of inducing an immune response in an individual and to novel compositions for performing the method of the invention and methods of making said compositions.

BACKGROUND OF THE INVENTION

The idiotypic determinants expressed on the cell surface immunoglobulin (Ig) of B-cell lymphomas can act as tumour-associated antigens (for review see George and Stevenson, 1989). As such they present an attractive target for therapy, notably for the administration of passive anti-idiotypic antibody to patients (Miller et al., 1982 New Engl. J. Med. 306, 517–522). Murine monoclonal antibodies (MAbs) raised against idiotypic determinants on B cell non-Hodgkin's Lymphomas (NHLs) have given limited benefit in human therapeutic trials. Partial and complete responses have been observed, but the murine MAbs tend to recruit human effector functions inefficiently and are themselves the target of a human anti-mouse antibody response. Also, outgrowth of surface Ig negative lymphoma cells has been observed following therapy (Levy et al., 1987 J. Immunol. Rev. 96, 43-; Bahler and Levy, 1992 PNAS 89, 6770–6774), although the complete loss of immunoglobulin expression is rare (Meeker, et al., 1985 New Engl. J. Med. 312, 1658 1665; Zelentz et al., 1990 Ann. Oncol. 2, 115–122). In light of these limitations, coupled with the cost and inconvenience of generating MAbs for individual patients, the approach has not been widely adopted. However, it is clear that anti-idiotypic antibodies do have therapeutic potential in lymphomas.

One alternative to passive anti-idiotypic serotherapy is active immunisation which aims to break tolerance and induce a strong anti-idiotypic antibody response in the patient. Since the response will be polyclonal, it is more difficult for the target B-cell to escape selection, and furthermore, the response will be present on a continuing basis, and so might be able to control residual disease. An additional advantage of this approach is that it also has the potential to stimulate T cell mediated immune responses against the lymphoma. Efforts to stimulate tumour immunity using modified tumour cell vaccines have met with limited success, but active immunisation with idiotypic Ig prior to tumour challenge has proved effective in suppressing model B-cell tumours (Stevenson and Gordon, 1983 J. Immunol. 130, 970–973; George et al., 1987 J. Immunol. 138, 628 634; Campbell et al., 1987 J. Immunol. 139, 2825–2833) in animals and to treat animals bearing incipient tumour (George et al., 1988 J. Immunol. 141, 2168–2174). Furthermore idiotypic immunisation with human Ig isolated from patients with lymphoma has been associated with sustained tumour regression (Kwak et al., 1992 New Engl. J. Med. 327, 1209–1215).

The problem is how best to present the antigen (the idiotypic antibody) to break tolerance and stimulate an effective anti-lymphoma immune response, and this remains a challenge. In addition, for lymphomas, which secrete little immunoglobulin, making the idiotype is a major problem. To make sufficient idiotypic antibody for immunisation heterohybridomas must be prepared by fusion with mouse cell lines and the antibody then purified (Carroll et al., 1985 J. Immunol. Methods 89, 61–67). The yield is frequently low and it must be subsequently confirmed that the fusion derives from the human B-cell tumour.

This latter problem has now been overcome; the use of recombinant DNA technology allows the $V_X$ and $V_L$ genes encoding the idiotypic determinant readily to be identified in patient biopsy material by PCR and sequencing (Hawkins et al, 1994 *Blood* 83:3279). These genes can be assembled as scFv for use as a DNA vaccine. This approach is based on the data coming from a range of infectious diseases where it is clear that DNA encoding sequences from pathogens can transfect cells directly and induce protective immune responses (Ulmer et al, 1993 259:1745; Davis & Whalen 1995, In *Molecular and Cell Biology of Human Gene Therapeutics.* Ed. George Dickson, Chapman & Hall, p368).

In previous work, in a mouse model for lymphoma, the V-genes of the tumour idiotope were cloned and expressed as light and heavy chain fusion proteins in bacteria. The separate chains were then used as immunogens. However the separate chains were denatured, and in any case were not co-expressed to provide the paratope of the antibody. Indeed the authors suggested that "future work on peptides with fixed configurations similar to epitopes present in the native protein may prove useful, as may the co-expression of both VH and VL genes in bacteria to produce a recombinant Fv protein" (Campbell et al., 1987, cited above). However the authors did not teach how to isolate the V-genes of the idiotope. Nor did the authors teach how to combine the recombinant Fv fragments into a vaccine.

SUMMARY OF THE INVENTION

In a first aspect the invention provides a nucleic acid construct for delivery into living cells in vivo for inducing an immune response in a patient to an idiotypic determinant present on a malignant B cell in the patient; the construct directing the expression of a fusion protein, said fusion comprising the idiotypic determinant and at least one T helper cell epitope from tetanus toxin.

Preferably the fusion protein will comprise a plurality of tetanus toxin epitopes, both B and T cell. Conveniently, the tetanus toxin epitopes are provided by inclusion in the fusion protein of tetanus toxoid Fragment C (FrC). Typically FrC will be placed on the carboxy side of the idiotypic determinant.

The idiotypic determinant is preferably present in the fusion protein in essentially the same conformation as that which it adopts on the surface of the patient's malignant B cells, thereby optimising the efficiency of the anti-idiotypic immune response induced by the construct. Conveniently this is achieved by expression of the idiotypic determinant within the context of a portion of an immunoglobulin (Ig) molecule or immunoglobulin-like molecule, such as a single chain Fv (scFv) fragment. The scFv fragment is particularly convenient, providing the necessary structural features of the idiotypic determinant with few extraneous amino acid residues. However, if desired additional amino acid residues could be included in the fusion protein, such as one or more constant domains (e.g. Syrengelas et al. 1996 Natural Medicine 2, 1038). Thus, for example, one could express the idiotypic determinant in the context of an entire immunoglobulin molecule.

In a preferred embodiment, the fusion protein is expressed with a leader sequence (recognised in human cells) which directs the fusion protein to the endoplasmic reticulum where the leader sequence is cleaved from the fusion protein. A large number of suitable leader sequences are known including, for example, the leader sequences (such as that for $V_H1$ described below) found at the 5' end of the human V genes. Such leader sequences have been found by the present inventors to increase the immunogenicity of the fusion protein. In principle, any other leader sequence is likely to exert an equivalent advantageous effect, but it is probable that those most similar to the natural immunoglobulin-type leader sequence will be optimal.

For the sake of convenience, the nucleic acid construct will preferably comprise a number of restriction endonuclease recognition sites. In particular, one or more such recognition sites may be located 5' of the sequence encoding the idiotypic determinant (conveniently between the optional leader sequence and the sequence encoding the idiotypic determinant), and one or more sites may be located 3' of the sequence encoding the idiotypic determinant (conveniently between the sequence encoding the idiotypic determinant and the epitope(s) from tetanus toxin). In this way, the same basic construct can readily be adapted to express different fusion proteins in which either the tetanus toxin portion or, more preferably, the idiotypic determinant, may be altered. Thus sequences encoding idiotypic determinants from different patients can easily be introduced into the construct.

In a particular embodiment this invention provides a vaccine nucleic acid which can be used in elicit an immune response against transformed human lymphocytes displaying an idiotypic marker, the nucleic acid encoding proteins comprising the heavy and light chain variable regions of an anti-idiotypic antibody displayed on surface of a malignant human B-cell.

In a second aspect the invention provides a method of making a nucleic acid construct for treating a patient suffering from a B cell malignancy, the method comprising:

(a) identifying a nucleic acid sequence encoding an idiotypic determinant present on the malignant B cells of the patient by analysis of a sample of cells from the patient;

(b) cloning the nucleic acid sequence encoding the idiotypic determinant; and (c) introducing the cloned nucleic acid into a vector, which vector allows for the idiotypic determinant to be expressed as a fusion with at least one T helper cell epitope from tetanus toxin.

Conveniently the nucleic acid encoding the idiotypic determinant is cloned from a sample of the patent's cells by PCR. A large family of suitable genetic PCR primers, capable of recovering nucleic acid sequences encoding essentially any B cell idiotypic determinant, is now available (Hawkins & Winter, 1992 Eur. J. Immunol. 22, 876). Typically the B cell malignancy is a lymphoma. Generally, the nucleic acid construct made by the method defined above will be in accordance with the first aspect of the invention.

In a third aspect, the invention provides for a method of treating a patient suffering from a B cell malignancy, the method comprising administering to the patient a nucleic acid construct in accordance with the first aspect of the invention defined above, so as to induce an immune response to the idiotypic determinant present on the surface of the patient's malignant B cells. B cell lymphomas are the conditions preferably treated by the method of the invention.

Preferably the nucleic acid sequence encoding the idiotypic determinant is cloned from samples obtained from the individual to whom it is delivered. Conveniently the nucleic acid sequence is delivered in unencapsidated form (i.e. not enclosed within a viral particle or other package). The nucleic acid may, however, be associated with the external surface of a package or particle (e.g. a liposome or a viral particle), which allows for the possibility of receptor-mediated delivery of the nucleic acid.

The fusion protein may direct the expression of the idiotypic determinant and the tetanus toxin epitope alone. Alternatively the fusion protein may additionally comprise further immunomodulatory polypeptide sequences, such as other foreign immunogenic proteins, or cytokines. Indeed it may be valuable to use several antigenic fusion partners to help prevent the theoretical problem that the immune response to the highly immunogenic moiety of the fusion protein could ultimately overwhelm any response to the relatively weakly immunogenic idiotypic determinant. Coat proteins of enveloped viruses and immunogenic cell surface or secreted proteins derived from any pathogenic organism or non-human species may be suitable for inclusion in the fusion protein.

An alternative modification is to design the nucleic acid construct so as to allow for the co-expression of the further immunomodulatory polypeptides as separate entities rather than as fusions with the idiotypic determinant/tetanus toxin epitope. Less preferably, the method of the invention could employ the use of a separate nucleic acid construct to express the further immunomodulatory polypeptides.

A number of cytokines are known to improve aspects of antigen presentation and the direct delivery of expression vectors containing cytokine genes could enhance vaccine efficacy. Interferon gamma is one example which could be useful due to the property of upregulating MHC expression (Gaczynska et al. 1993 Nature 365, 264–267). Another polypeptide which could be expressed by the vaccine nucleic acid is granulocyte/macrophage-colony stimulating factor (GM-CSF). The relevant gene could be encoded on the same, or on a separate, vector and the amount of polypeptide expressed varied independently.

One advantage of the genetic approach to vaccination is that it potentially allows efficient use of the natural method of presenting antigen which should therefore engage a wide range of effector systems. Moreover, manipulation and improvement of the response obtained should be relatively easy; for example, it may be possible to improve the efficiency of presentation of antigen to T cells by expressing molecules with co-stimulatory activity together with the immunogen. One important molecule involved in co-stimulation is B7, which interacts with CD28 expressed by T cells thereby providing accessory signals for T-cell activation (Galvin et al., 1992 J Immunol 12 3802–3808). Vectors could be constructed which express both B7 and the idiotypic Ig. Sequences of both mouse and human B7 are published (Freeman et al., 1989 J. Immunol. 8 2714–2722) and the genes may readily be cloned by PCR.

It is thus an optional feature of the present invention that the method further comprises the delivery of a second nucleic acid sequence to the individual which directs the expression of a further immunomodulatory polypeptide for the purpose of further modulating the immune response to the idiotypic determinant. This second nucleic acid sequence may be comprised on the same nucleic acid molecular as the first nucleic acid sequence, or may be present on a second nucleic acid molecule.

Methods of introducing the nucleic acid construct into living cells in vivo are now well-known to those skilled in the art. Conveniently the nucleic acid is simply injected as naked DNA into the patient (typically intramuscularly) as a mixture with a physiologically acceptable diluent, such as a saline solution. Details of some suitable methods and preferred embodiments of the administration of the nucleic acid construct into a patient are described in U.S. Pat. Nos. 5,580,859 and 5,589,466. More involved methods of gene transfer include the use of viral vectors, encapsulating the DNA into liposomes, coupling of DNA to cationic liposomes or to the outside of viruses (for review see Miller, 1992 Nature 357, 45–46). These have the advantage of increased efficiency of transfer but, by comparison with direct injection of purified plasmid DNA, these alternative approaches are somewhat involved and raise more safety issues.

In a fourth aspect the invention therefore provides a composition for use in the method of treating a patient suffering from a B cell malignancy (according to the third aspect of the invention defined above), the composition comprising a nucleic acid construct directing the expression of a fusion protein, said fusion protein comprising an idiotypic determinant which is present on the malignant B cells of the patient and at least one T helper cell epitope from tetanus toxin, together with a physiologically acceptable diluent or carrier.

In a particular embodiment the present invention entails the isolation of the V-genes from the tumour B-cells to express the idiotope (and paratope) of the tumour antibody. Thus starting with a sample of B-cells from the patient, the rearranged V-genes of both heavy and light chains are amplified using the polymerase chain reaction and generic "universal" primers (Orlandi et al., 1989 PNAS 86 3833–3837; Marks et al., 1991 J. Mol. Biol. 222, 581–597; see also Table 1, Seq. ID Nos. 1 48). The amplified V-genes are cloned and then sequenced (Sanger et al., 1977 PNAS 74, 5463–5467). These from the malignant B-cells are identified as predominant repeated VH and VL gene sequences. In several patients, and for both heavy and light chains, it was possible to identify a common repeated sequence. The combination of the heavy and light chains identifies the idiotope of the tumour (Example 1). In principle, it would also be possible to amplify and link the rearranged V-genes within the same cell (Embleton et al., 1992 Nucl. Acids Res. 20, 3831–3837) to identify a major combination of linked heavy and light chain sequences that identify the idiotope but here the VH and VL are separately identified and then linked by PCR assembly. The VH and VL genes are cloned into vectors for the expression of both V-domains as a functional antibody fragment, for example as a linked single chain Fv fragment (see below).

Ideally a vaccine should be capable of stimulating antigen-specific B cells, cytotoxic T lymphocytes (CTLs) and helper T cells. B cell stimulation requires that the target antigen should bind with sufficiently high affinity to specific antigen receptors (surface Ig) on the B-cell surface. Certain multivalent antigen can stimulate B cell proliferation directly but more often, and to provide an effective anamnestic response, there is a requirement for additional signals provided by helper T cells (see below). In the present invention, T cell help is recruited by expressing the idiotypic determinant as a fusion protein with at least one T helper cell epitope from tetanus toxin.

The T cell receptors (TCRs) of CTLs recognise specific MHC class I-associated peptides displayed at the target cell surface. Such peptides are generally derived by processing of larger polypeptides or proteins manufactured within the target cell. Thus, for efficient CTL stimulation the target antigen should be synthesised intracellularly in MHC class I-expressing cells. The level of expression should be high enough to generate sufficient peptide to displace those self peptides which are normally bound (possibly with higher affinity) in the MHC peptide-binding groove (Ohno, 1992 PNAS 89 4643–4647). Similar to antigen-specific B-cells, for proliferation and increased cytotoxic capability, CTLs require additional signals (in the form of cytokines) following antigen recognition and these are provided by helper T cells.

CD4-positive helper T cells interact (via their unique TCRs) with specific cell surface MHC class II-associated peptides and such peptides are generally derived by proteolytic cleavage of protein antigens internalised by specialised antigen presenting cells (APCs). Macrophages, dendritic cells and B lymphocytes are amongst the cells which can present antigen in this way. Thus, B lymphocytes internalise and process antigen bound to their surface Ig and subsequently present MIIC class II-associated derivative peptides. CD4-positive T helper cells recognising the surface peptide can then release various immunostimulatory cytokines and stimulate further B cell activation, proliferative and antibody production. Similarly, macrophages present at the site of a local inflammatory response can process phagocytosed antigen and stimulate cytokine release by T helper cells, leading to enhanced activation, proliferation and cytotoxicity of locally resident CTLs.

The vaccine antigen should therefore ideally 1) be synthesised intracellularly by MHC class I-positive host cells, 2) give rise to peptides which, displayed by host cell class I MHC can stimulate a subset of host CTLs via their TCRs, 3) give rise to peptides which, when displayed by host cell, class II MHC can stimulate a subset of host helper T cells via their TCRs, 4) be internalised and processed by host APCs including both macrophages and antigen-specific B cells, 5) be available in its native form for interaction with host B lymphocytes.

In a further specific embodiment, the invention provides for the expression of the rearranged VH and VL genes of the idiotype of the tumour antibody within mammalian cells, allowing the production of peptides for display on the cell surface in combination with host MHC, and for display (or secretion) of the paratope (as a folded antibody fragment), to trigger the production of anti-idiotypic antibodies. The antibody fragments could be introduced into mammalian cells by infection with a recombinant virus encoding the antibody fragments.

In principle, the antibody fragments could be provided with a signal sequence for their secretion or display on the surface of the infected (transfected) cell. Alternatively the fragments could be linked to another protein that is displayed on the surface of the cell, for example a viral coat protein, as described in Example 2. The antibody fragments (as single chain Fv fragments) are displayed in a functional form attached to the coat protein of a virus, indicating that they are also folded and in a native form on the surface of an infected cell (Russell et al., 1993 Nucl. Acids Res. 21, 1081–1085).

The antibody fragments could also be introduced into mammalian cells using nucleic acid encoding the antibody fragments. For example, a gene encoding a fusion protein between a viral coat protein (as above) and the antibody fragments may be used to immunise mice by direct injection (e.g. subcutaneous or intramuscularly).

The invention will be further described by way of example and by reference to the drawings, of which:

BRIEF DESCRIPTION OF THE DRAWINGS

FIG. 2 shows the sequence of vectors used to express and purify scFv idiotypic immunoglobulin (SEQ ID NOS:59–62);

FIG. 5 shows the sequence of a HindIII—XbaI fragment of the vector pVAC1 (SEQ ID NOS:56–57);

FIG. 7 shows the entire sequence of the vector pVAC1 (SEQ ID NO:58);

FIGS. 11a and 11b show the results FACS analysis described in example 2;

EXAMPLES

Example 1

Figure 1:
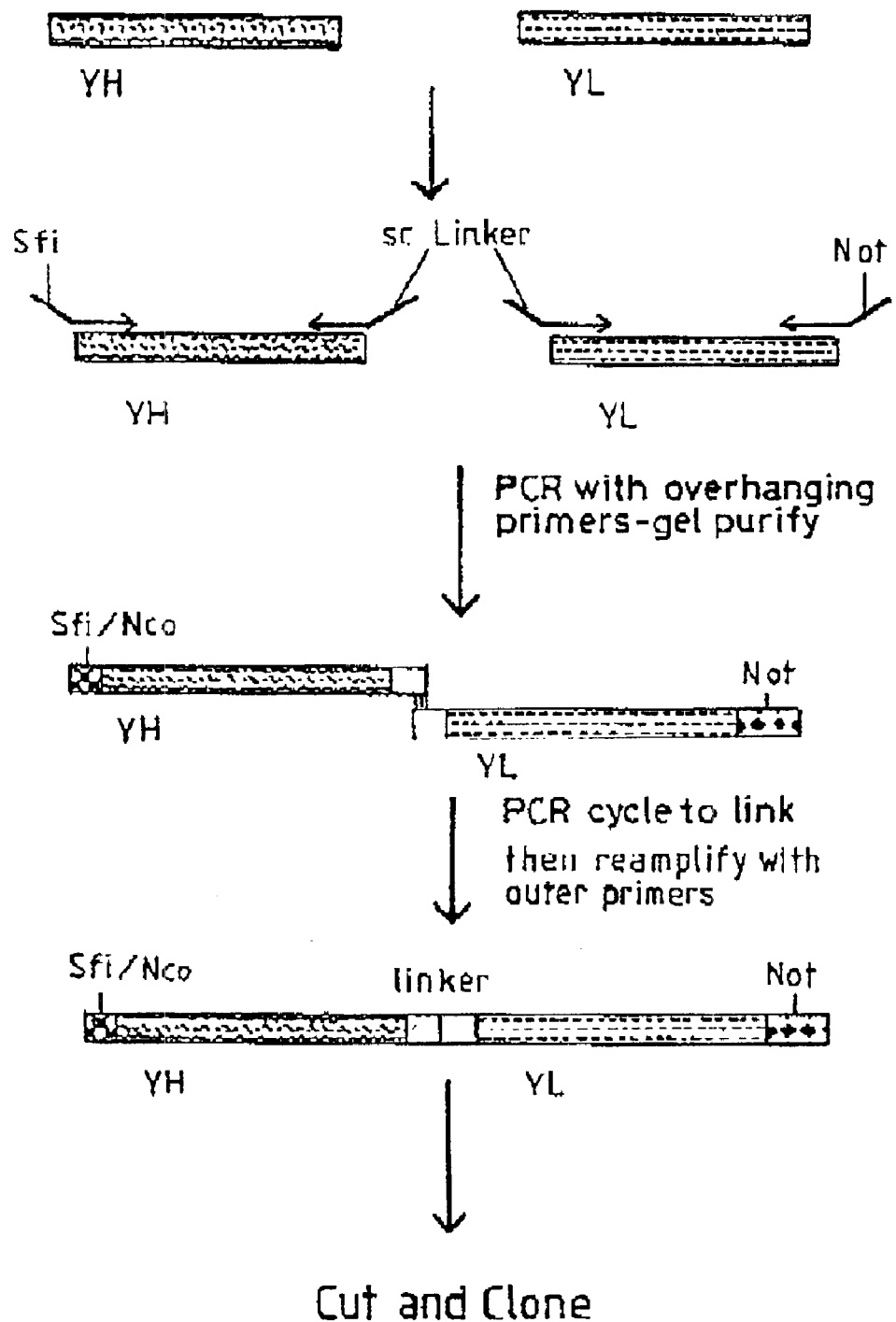
FIG. 1 is a schematic representation of the method of PCR assembly of DNA expressing scFv.

Indentification of V-genes from Biopsies of B-cell Lymphoma

Preparation of Biopsy Material

Biopsy specimens were obtained from five patients with pathologically confirmed Follicular Lymphoma. They were obtained during routine diagnostic procedures. The light chains were identified as kappa or lambda by immunohistochemistry. As non-malignant controls, a small bowel lymph node from from a patient with Crohn's disease and a sample of spleen from a patient undergoing splenectomy were obtained. Biopsy material was prepared as a single cell suspension and the cells subsequently frozen and stored at −70° C.

Preparation of DNA for PCR

For PCR the DNA was prepared using a simple proteinase K/Tween 20 lysis method (Innis et al., 1990 PCR Protocols: A Guide to Methods and Applications: Academic Press Inc., p147). Briefly the cells were pelleted by centrifugation for 20 seconds at 13,000 rpm in a microcentrifuge. The cells were then washed twice with 1 ml PBS before resuspending at approximately $10^6$/ml in K-buffer (10 mM Tris.Cl (pH 8.3), 50 mM KCl, 1.5 mM MgCl$_2$, 0.5% Tween 20, 100 mg/ml proteinase K) and incubated at 56° C. for 60 minutes to lyse the cells and release DNA. The proteinase K was then reactivated by incubation for 30 minutes at 95° C. DNA thus released was used directly in the PCR reactions or stored for subsequent use at −20° C.

PCR Primers

PCR primers were designed to amplify re-arranged heavy chain kappa and lambda light chain genes. The 5'primers are based on framework 1 of the V-genes. The VH and VL primers are similar to those described by Marks et al. (1991). However, for amplification from genomic DNA (as opposed to cDNA) the product was found to be cleaner if primers shortened by one base at the 3' end were used (data not shown). In addition, the number of primers used was reduced by combining similar primers as one consensus primer. With the exception of one change in the JH primers, to introduce a common BstEII site, changes were not made to introduce restriction sites.

Limited DNA sequences information was available on which to base the Vλ primers but primers were made to Vλ1, Vλ2, Vλ3 and Vλ4 families from the available sequence data (Songsivilai, et al. 1990 Eur. J. Immunol. 20, 2661–2666; Alexandre et al., 1989 Nucl. Acids Res. 17, 3975; Bernard et al. 1990 Nucl. Acids Res. 18, 7139; Chuchana et al., 1990 Eur J. Immunol. 20, 1317–1325). Other families are known to exist (Chuchana et al., 1990) but there were no nucleotide sequence data available and so primers were not made. J-region primers were made to be complementary to the genomic sequence of the germline J-regions for heavy chain (Ravetch et al., 1981 Cell 27, 583–591), kappa chain (Hieter et al., 1982 J. Biol. Chem. 257, 1516–1522) and lambda chain (Udey and Blomberg 1987 Immunogenetics 25, 63–70; Dariavach 1987 PNAS 84 9074–9078; Bauer and Blomberg 1991 J. Immunol. 146 2813–2820; Combriato and Klobeck, 1991 Eur. J. Immunol. 21, 1513–1522; Frippiat, 1990 Nucl. Acids Res. 18, 7134). The Jλ genes combine with their respective Cλ genes and thus since Cλ4, Cλ5 (Dariavach, 1987) and probably Cλ6 (Bauer and Blomberg, 1991; Combriato and Klobeck, 1991) are pseudogenes they should not appear as expressed protein. As a result primers to these Jλ genes were not made. By combining two J region primers, in all three J1 primers were made Jλ1, Jλ2/3, Jλ7. Table 1 gives a full list of the primary PCR primers used in example 1.

PCR Amplification of Rearranged Immunoglobulin Variable Regions

The V-gene family and J-region primers were used as equimolar mixes of the individual primers shown in Table 1. VHBACK and JHFOR mixes were used for the heavy chain PCR reactions. Similar mixes were used for kappa or lambda chain PCR amplification.

PCR amplification was performed in 50 ml volume using Hybaid Thermal Reactor (Hybaid). Reaction mixtures containing 20 pmol of each primer mix, 250 mM dNTPs (Pharmacia, Uppsala, Sweden) in 1×PCR buffer (Promega, 10 mM Tris.Cl[pH8.8], 50 mM KCl, 1.5 mM MgCl$_2$, 0.1% Triton X-100). To minimise any risk of contamination extensive precautions were taken. The mixes were set up in a laminar flow hood in a room designated specifically for setting up PCR reactions. The samples were then UV treated for 5 minutes in a UV oven (Amplitad, Genetic Research, Dunmow, UK). The template (5 ml) was then added, the reaction mix was then overlaid with mineral oil (Sigma) and the sample heated to 94° C. for 5 minutes. At this stage Taq DNA polymerase (Promega), 2.5 units, was added. Amplification was performed using 35 cycles, 94° C. 1 min, 65° C. 1 min annealing; 72° C., 1 min elongation.

Amplified variable regions were analysed on a 1.5% LMP agarosc/TAE gel and visualised with ethidium bromide. The band of size 320/350 base pairs was excised and purified using a GENECLEAN II kit (Bio101) according to the manufacturers instructions. At least two independent PCR amplifications of V regions were performed from the sample of every patient and the PCR of lymph node DNA was performed before the corresponding PCR from the heterohybridomas (which were also available).

Cloning and Sequencing of PCR Products

The T-vector cloning system described by Marchuk (Marchuk et al, 1991 Nucl. Acids Res. 19, 1154) was used. In belief, the vector was prepared from pBluescript II KS+ (Stratagene) by digestion with EcoRV (from NBL) to produce blunt ends and then treatment with Taq DNA polymerase (Promega) in PCR buffer (Promega) containing 2 mM dTTP at 70° C. for 2 hours. The purified V-gene PCR product was ligated into the T vector and transformed into competent E. coli—strain TG1 (Gibson, 1984 Ph.D. thesis, University of Cambridge, United Kingdom). Recombinant clones were identified by blue/white selection using isopropyl-β-thiogalactosidepyranoside (IPTG, Sigma). Random recombinant clones were picked and ssDNA prepared after superinfection with helper phage (M13KO7, Stratagene) (Vieira and Messing, 1987 Methods Enzymol. 153, 3–11). The clones were sequenced by the dideoxy method (Sanger et al., 1977) using T7 DNA polymerase (Sequenase, USB, Cleveland, USA). A number of clones from each patient were sequenced and the sequences compared.

Assembly of Tumour V-genes as scFv

The assembly method, illustrated in FIG. 1 is based on that described by Davis et al., (1991 Bio/Technology 9, 165–169). The assembly process uses a second set of primers. The VHSfiBAK primers encode SfiI cloning site and also hybridise to the original set of VHBAK primers. The scJHFOR and scVk/vλ BAK primers hybridise to their respective initial primers but also encode the sc linker to allow production of a single chain Fv (scFv) (Huston et al., 1988 PNAS 85, 5879–5883).

The NotJk/IFOR primers hybridise to their respective initial primers but also include the NotI restriction site. These primers are also summarised in Table 1. The assembly is carried out in two stages. First the V-genes (heavy and light chains) were amplified from the sequencing template using the new set of oligonucleotides. The PCR mixture was made up as above but the primers used were only the relevant V-gene family and J-region primers identified by previous sequencing. Template was 0.100 ng of ssDNA sequencing template. The PCR conditions were 94° C. for 1 minute, 50° C. for 1 minute, 74° C. for 1 minute with 10 cycles of amplification. At the completion of the PCR the further dNTPs were added (5 ml of 2.5 mM stock solution) with Klenow polymerase (Boehringer, 2.5 units) and then incubated at 20° C. for 15 minutes to produce blunt ends.

Following this step the product was gel purified as above and resuspended in 25 ml water. Then 5 ml from the heavy and 5 ml from the light chain product were used in the assembly. For this process the PCR reaction was carried out in two steps. Initially no primers were added and the following cycles were used: 94° C. for 1 minute, 50° C. for 1 minute, 74° C. for 1 minute for 7 cycles to join the heavy and light chains. During the secondary PCR described above the heavy chain and light chain are tagged with primers encoding the single chain linker. This tag contains 15 nucleotides on each of the heavy and light chains complementary to each other and thus allows them to anneal to each other. During the extension reaction full length joined scFv molecules are formed. At the end of these 7 cycles the temperature is held at 94° C. for 3 minutes and the relevant outer primers (SflVHBACK/NotJFOR) added for the "pull-through" amplification. This amplification consists of 10 cycles: 94° C. for 1 minute, 74° C. for 2 minutes an serves to amplify the small amount of linked product formed.

Cloning for Expression, and Expression and Purification of scFv

After assembly the scFv was digested with SfiI/NotI as described (Marks et al., 1992) and cloned into a scFv expression vector (Hawkins et al., 1992 J. Mol. Biol. 226, 889–896) based on pUC119 (Vieira and Messing, 1987). A new expression vector, pRH2, which has the Myc Tag replaced by a hexahistidine tag was made to allow purification using metal affinity chromatography. This was made by inverted PCR site directed mutagenesis (Hemsley et al., 1989 Nucl. Acids Res. 17, 6545–6551). The vectors are shown in Figure (2 Seq. ID Nos. 59–62).

To check for expression of full length scFv individual colonies were picked and grown for four hours with constant shaking in 1 ml 2×TY/0.1% Glucose/100 mg/ml Ampicillin at 30° C. At the stage 1PTG: was added to a final concentration of 1 mM and shaking continued for 18 hours. Supernatant was harvested by centrifugation at 13,000 rpm in a microcentrifuge for 5 minutes. The bacterial pellet was frozen at 20° C. for preparation of plasmid DNA and the supernatant was analysed by Western blotting using the 9E10 anti-Myc antibody (Waul et al., 1989 Nature 341, 544–546). Plasmid DNA was then prepared from the bacterial pellet of colonies thus shown to express full length scFv. From this plasmid preparation the scFv was subcloned as an SfiI/NotI fragment into pRH2 One liter cultures of bacteria were grown with constant shaking in 2 liter flasks containing 2×TY/0.1% Glucose/100 mg/ml Ampicillin at 30° C. to an A600 nm of 0.9. At this stage IPTG was added to a final concentration of 1 mM and the incubation continued for a further 4 hours. The bacteria were then pelleted by centrifugation and the periplasmic fraction was prepared as described by Skerra et al., (1991 Bio/Technology 9, 273–278).

The scFv antibody fragment was purified from the periplasmic fraction utilising the hexahistidine tag. The method is based on that described by Skerra et al., (Skerra et al., cited above) but it was found that the use of six histidines and nickel rather than five histidines and zinc was preferable (data not shown). The periplasmic preparation from a 1 liter culture was loaded onto a 1 ml column of Chelating Sepharose Fast Flow (Pharmacia) previously coupled with nickel ions according to the manufacturers instructions. The column was then washed with 10 ml of PBS/1 M NaCl (pH 7.2) followed by 5 ml PBS/1 M NaCl/75 mM Imidazole (pH7.2). The retaining scFv was then eluted with 5 ml PBS/1 M NaCl/300 mM Imidazole (pH 7.2) and collected as 1 ml fractions. The peak protein fractions were identified by determining the A280 nm and these were then dialysed against PBS before analysis by SDS-PAGE.

PCR, Cloning and Sequencing of V-genes from Follicular Lymphoma and Normal Lymph Node The PCR amplification from the DNA of biopsy specimens was successful in all cases apart from the lambda light chain from patient number 5. A number of clones from each patient were sequenced. Analysis of the sequences derived from the reactive lymph node and from the normal spleen revealed that there were no repeated sequences. From each of the tumour bearing lymph nodes there were single repeated sequences. A summary of the sequencing results is shown in Table 2. Amongst the repeated sequences there were up to two base changes which were presumed to result from PCR errors. Nevertheless a consensus sequence was readily apparent and in each case there were clones with this consensus sequence. To confirm the sequence a second independent amplification was performed and further V-genes sequenced. The same consensus sequence was identified. The repeated V-gene sequences suggest clonal expansion and thus identifies the tumour V-gene. For three of the five tumour biopsies analysed here a heterohybridoma was available. PCR amplification, cloning and sequencing confirmed the sequence identified direct from the lymph node.

The absolute percentage of the tumour derived V-gene varied and there are several reasons for this. First, the biopsies vary in the degree of tumour infiltration (although in all cases examined here malignant B-cells comprise >50% of the total cells present). Second, the primers will vary in the efficiency with which they amplify any particular gene—in extreme cases as with the lambda light chain in patient 4 a chain may not amplify at all. Third, some pseudogenes can be amplified by these primers and this may reduce the overall percentage of tumour derived V-genes.

Assembly, Expression and Purification

The use of PCR assembly avoids the use of multiple restriction enzymes which may cut V-genes at internal sites. This process used here appears efficient and does not require the separate preparation of a linker fragment (Clackson et al., 1991 Nature 352, 624–628). To check the assembly process the linked product was cloned into an expression vector which included the Myc Tag (FIG. 2). Randomly picked clones were grown up and induced as previously described (Hawkins and Winter, 1992). Western Blotting using a monoclonal antibody, 9E10, against the Myc Tag (Ward et al., 1989) demonstrated that 80% of the clones correctly expressed. For case of purification the scFv frgament was subcloned into the expression vector pRH2 containing a hexahistidine tag. A clone from patient 5 was grown up in a 1 L volume the scFV fragment purified from the periplasm. The yield was estimated as 0.5 mg/L/OD600 based on an A280 nm of 1.4 for a 1 mg/ml solution.

Example 2

Construction of a Fusion Protein

Plasmid Construction

The BamHI/ClaI env fragment (nt 6537–7674, nt numbering from Shinnick et al, 1981 Nature 293, 543–548) from pCRIP (gift from O. Danos, Danos & Mulligan 1988 PNAS 85, 6460–6464) was cloned into the BamHI/ClaI backbone fragment of pZipNeoSV(X) (gift from R. Mulligan, Cepko et al., 1984 Cell 37, 1053–1062 to generate an intermediate plasmid penvBam/Cla.

A SfiI/NotI cloning site was introduced beyond the leader peptide sequence between codons corresponding to the 6th and 7th aminoacids (from the N-terminus) in the mature MoMLV env polypeptide. The oligonucleotide pair envNotrev (5'-CTG CAG GAG CTC GAG ATC AAA CGG GCG GCC GCA CCT CAT CAA GTC TAT AAT ATC-3', Seq ID No. 49, complementary to MoMLV env nts 5894–5914 with a 33nt 5' overhang encoding a NotI site and 21nt complementary to the 5' tail of envSfifor) and envseq7 (5'-GCC AGA ACG GGG TTT GGC C-3'. Seq ID No. 50, reverse complement of MoMLV env nts 6581–6600) was used to prime amplification (from plasmid pCRIP) of a 739bp fragment downstream of env codon 6. A second oligonucleotide pair, envSfifor (5'-TTT GAT CTC GAG CTC CTG CAG GGC CGG CTG GGC CGC ACT GGA GCC GGG CGA AGC AGT-3', Seq ID No. 51, reverse complement of MoMLV env nts 5873–5893 with a 36nt 5' overhang encoding a SfiI site and 21nt complementary to the 5' tail of envNotrev) and revMLVpo1 (5'-AAT TAC ATT GTG CAT ACA GAC CC-3', Seq ID No. 52, complementary to MoMLV pol nts 5277–5249) was used to prime amplification (from pCRIP) of a 702bp fragment upstream of env codon 7. Amplifications were carried out using Vent polymerase and reactions were subjected to 15 PCR cycles at 94° C. for 1 min, 60° C. for 1 min and 72° C. for 1 min. The complementary 21nt tails of the 702 and 739bp gel-purified PCR products allowed PCR linkage to generate an env gene fragment incorporating a SfiI/NotI cloning site at the desired position. The two fragments were mixed and subjected to three PCR cycles (94° C., 40° C., 72° C. for 1, 1, and 2 minutes respectively) followed by 17 further cycles of amplification (94°, 60°, 72° for 1, 1 and 2 minutes respectively) after addition of oligonucleotides envseq7 and BgIenvrev (5'-TAA TCA CTA CAG ATC TAG ACT GAC ATG GCG CGT-3', Seq ID No. 53, complementary to MoMLV pol nucleotides 5766 to 5785 with the 5' tail incorporating a bg1II restriction site).

Figure 3:
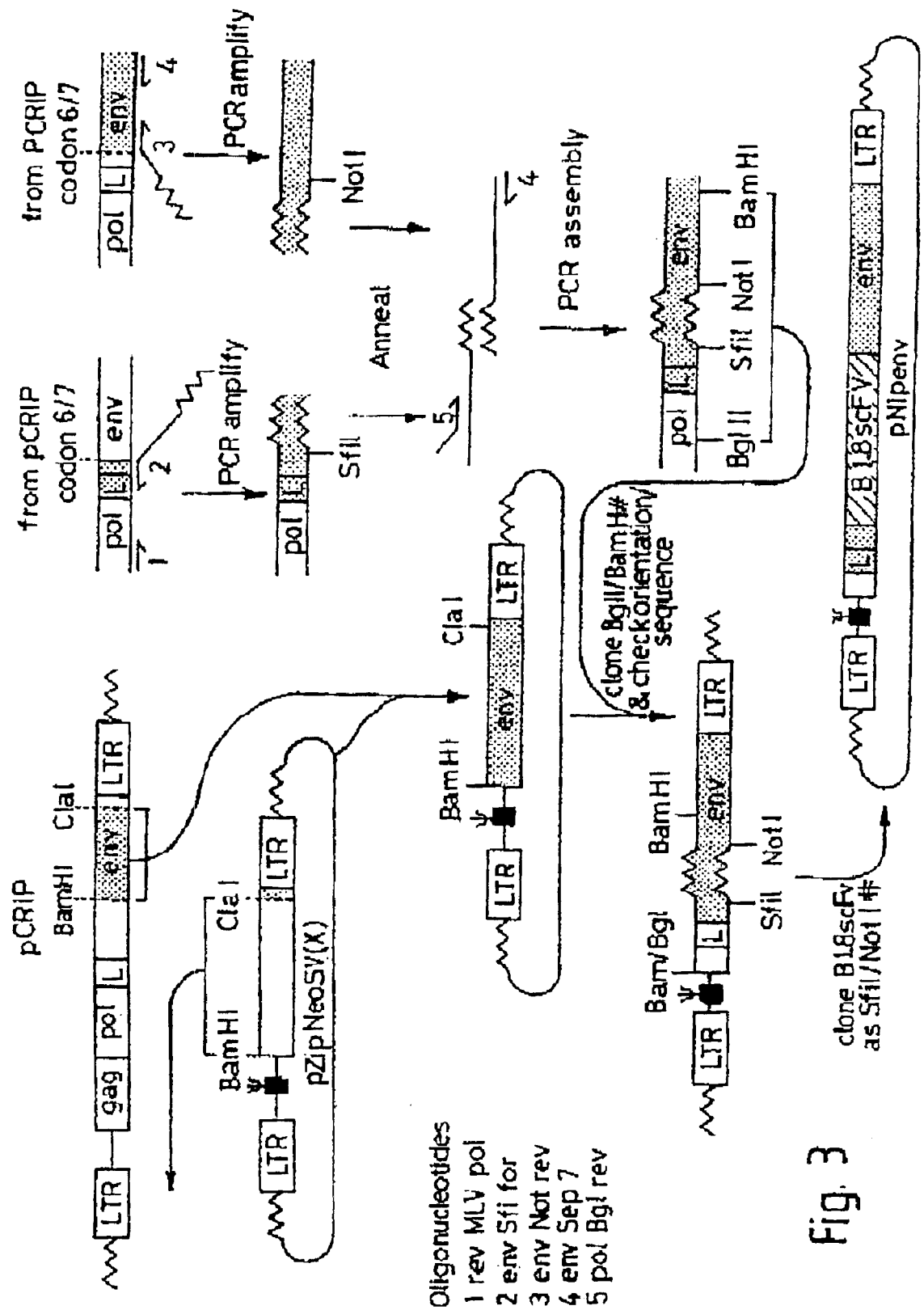
FIG. 3 is a schematic representation of the method used to produce plasmid pNipenv.

The product, a 905bp fragment, was digested with BglII and BamHI and cloned in forward orientation into the BamHI site of penvBam/Cla (see above) giving the plasmid pSfi/Notenv. Correct assembly of this plasmid was confirmed by restriction analysis and dideoxy sequencing (Sanger et al., 1977 PNAS 74, 5463–5467). A functional B1.8 scFv antibody was then subcloned from prokaryotic expression vector (Hawkins et al., 1992 J. Mol, Biol. 226, 889–896) as an SfiI/NotI fragment into the SfiI/NotI cloning site of pSfi/Not.Env to generate the plasmid pNIP env (FIG. 3). The sequence across the junctions of pNIPenv is show in FIG. 4 (Seq. ID No. 63 to 66, including translation of nucleotide sequence).

Figure 4:
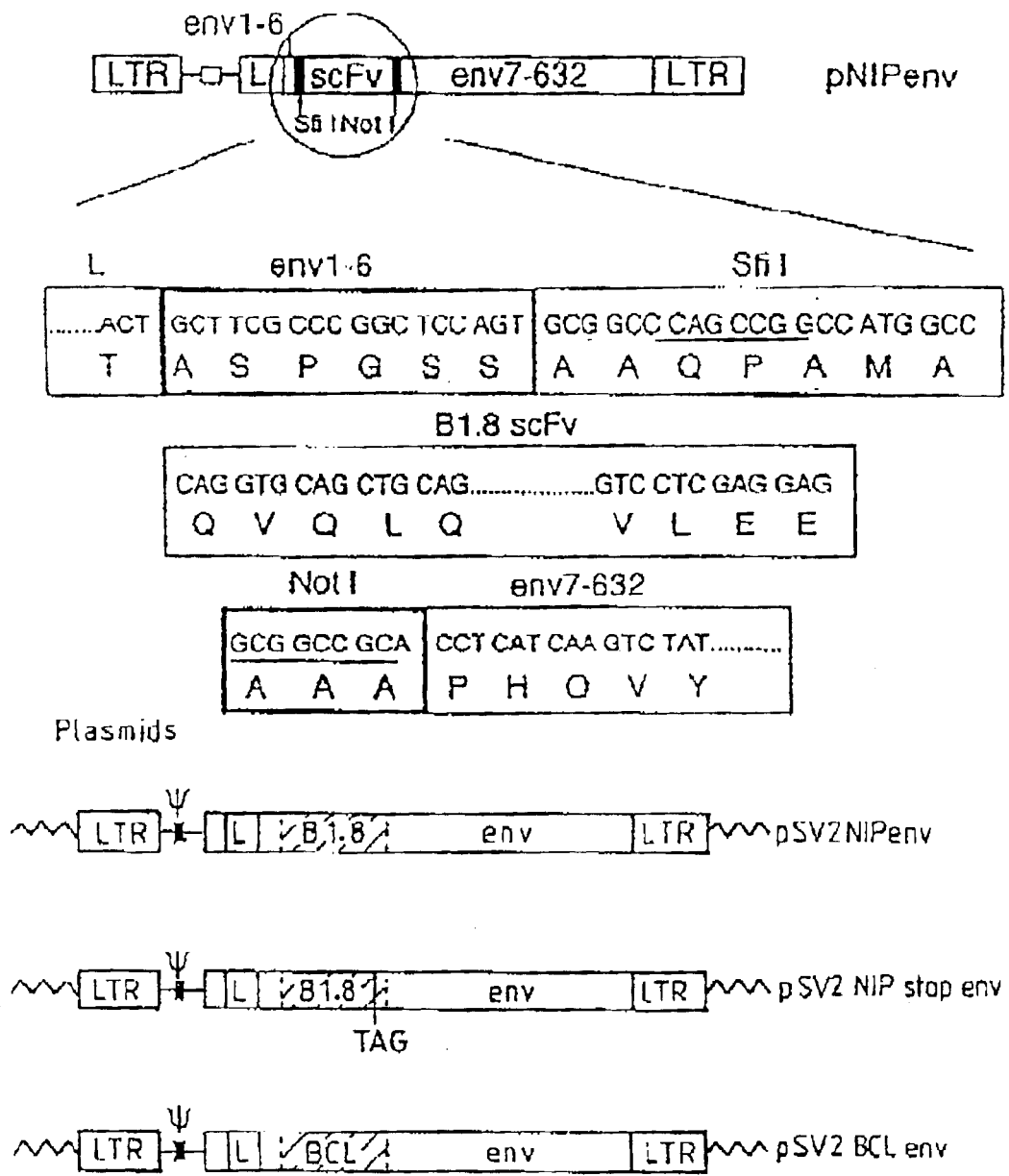
FIG. 4 is a schematic representation of the plasmid constructs pNipenv, pSV2 Nipenv, pSV2 Nip stop env, and pSV2 RCL env (SEQ ID NOS:63–66)

Finally, the modified retroviral envelope expression cassette was subcloned as a HindIII/EcoRI fragment into a modified pSV2Neo plasmid (a gift from Ashok Venkharaman. MRC Centre, Cambridge) to generate the plasmid pSVNIPenv (FIG. 4).

Cell Transfection

NIH3T3 fibroblasts and the ecotropic retroviral packaging cell line psi2 (Mann et al., 1983 Cell 33, 153–159) were maintained in DMEM/10% FBS supplemented with 60 µg/ml benzylpenicillin and 100 µg/ml streptomycin at 37° C. in atmosphere of 5% $CO_2$. The cells were replated twice weekly using EDTA without trypsin to disrupt the monolayer.

Plasmid pNIPenv was transfected (with pDCneo, a plasmid containing a neomycin resistance marker) into psi2 cells by calcium phosphate precipitation. Briefly, $2 \times 10^5$ cells were plated in 90 mm tissue culture plates (Nunc), cultured overnight, washed and fed with 10 mls new medium. 10 µl plasmid DNA and 50 µl 2 M $CaCl_2$ (0.2 µm-filtered) were diluted in sterile water to a volume of 400 µl. The $CaCl_2$/DNA mix was added dropwise to an equal volume of 0.2 µm-filtered 2×HEPES-buffered saline (280 mM NaCl, 10 mM KCl, 1.5 mM $Na_2HPO_4.2H_2O$, 12 mM dextrose, 50 mM HEPES, pH adjusted to 7.05 with 0.5 N NaOH) and left to stand for 20 minutes at RT. The transfection solution (800 ml) was added to the cells which were cultured for 16 hrs, washed and refed. G418 selection (1 mg/ml) was commenced 24 hrs later and continued for approximately 2 weeks.

Transfected colonies expressing surface B1.8 single chain antibody were identified by panning with NIP.BSA-coated beads. Briefly, Tosyl activated paramagnetic beads (Dynal, Oslo, Norway, Prod. no. 14004) were coated with NIP 10.BSA (approximately 10 NIP-caproate-O-succinimide molecules coupled to each bovine serum albumin molecule, Hawkins et al., 1992), washed extensively in PBS and blocked with DMEM/10% FBS. 90 mm tissue culture plates containing up to 50 G418-resistant psi2 colonies were rocked gently for 1 hr at 40° C. followed by 1 hr at room temperature with 2×10⁷ (50 µl) beads in 5 mls DMEM/10% FBS. After 5 washes in PBS, positive colonies (heavily coated with paramagnetic beads) were easily identified and were transferred individually for further expansion, cryopreservation and harvest of cell supernatants.

Therefore it was shown that the specificity of the antibody is displayed on the surface of the cells, and therefore that the antibody is folded.

Constructions of a Soluble Protein Expression Vector

To create a soluble expression vector a stop codon and frame shift mutation were inserted between the antibody gene and the 3' portion of the MoMLV Envelope gene. The B1.8 scFv fragment was PCR-amplified (10 cycles, 94° C. 1 min, 55° C. 1 min, 74° C. 1 min) using SfiVHBAK (5'TAC TCG CGG CCC AAC CGG CCA TGG CCC AGG TSM ARC TGC AGS AGT C-3', Seq ID No. 54) and a forward primer Not.STOP (5'-AAC AGT TTC TGC GGC CGC CTC CTC AGA GGA C-3', Seq ID No. 55) encoding the nucleotide insertion to create a stop codon and frameshift 5' of the NotI site. The fragment was then digested with SfiI/NotI and cloned into pSfi/Not.Env to create the plasmid pNIPstop (FIG. 4). Plasmid pSVBCLenv (FIG. 4) was derived from pSVNIPenv by replacing the B1.8 scFv with a control scFv gene which was PCR-cloned from the BCL1 mouse lymphoma. VH and Vλ genes were PCR cloned and assembled from BCL-derived DNA using standard protocols.

Preparation of Plasmid DNA

Plasmids were amplified in *E. coli* strain TG1 (Gibson, 1984), extracted by alkaline lysis and column purified using the Promega Magic Maxipreps™ DNA purification system (Promega, Madison, Wis. USA). The DNA was eluted in water. The purity of the plasmid prep was confirmed by agarose gel electrophoresis and by measuring the A260 nm/A280 nm ratio (in all cases the ratio was >1:7). The purified plasmid was stored at −20° C. Prior to use the plasmid was adjusted to 160 mg/ml in 200 mM NaCl.

Preparation of B1.8 scFv Protein

For bacterial expression, the B1.8 scFv gene was cloned as a PstI/NotI fragment into the vector pRH2, which links a tail of six histidines to the C-terminus of the scFv and was derived by inverse PCR mutagenesis. This plasmid was transformed into *E. coli*, strain TG1 and the scFv protein expressed and purified on an NP-sepharose column as previously described (Hawkins and Winter, 1992 Eur. J. Immunol. 22, 867–870). The purified protein was shown to bind strongly to NIP-BSA using a previously described ELISA (Hawkins and Winter, 1992). As a negative control scFvD1.3 (Hawkins et al., 1992) was cloned into the expression vector pRH2 and expressed and then purified on a lysozyme column as described by Hawkins et al., (1992, cited previously).

Vaccination Protocol

Male BALB/c mice 10 weeks of age were used for immunisation. Pre-immunisation blood samples were obtained by tail bleeds. The blood was centrifuged at 13,000 rpm for 2 minutes in a microcentrifuge to separate the serum. The serum then stored at −20° C. for subsequent assay. Two groups of mice were immunised some with DNA and some with protein. The two groups were immunised as described below.

a) Protein vaccine: 1.8 scFv protein was adjusted to a concentration of 250 mg/ml in PBS and mixed with an equal volume of CFA. Mice were challenged subcutaneously with 100 ml of this vaccine (12.5 mg scFv) at two separate sites. Identical boosts were administered two and four weeks later. 200 ml tail bleeds were obtained 10 days after the final boost. Blood samples were processed as above.

b) DNA vaccine: Two groups of three mice were challenged with 50 ml (8 mg) DNA, either subcutaneously (sc) in both flanks, or by the intramuscular (im) route (right and left quadriceps, total DNA for each mouse 16 mg). Two identical booster inoculations were given at one week intervals. 200 ml tail bleeds were obtained immediately prior to the first, second and third challenge and one week after the final boost. Serum was separated and stored as aboved.

Analysis of Immune Response

Individual flat-bottomed wells in flexible 96 well assay plates (Falcon 3912 Micro Test III) were coated with B1.8.His or control (D1.3 His anti-lysozyme) scFv protein at 25 mg/ml overnight in PBS at room temperature. The use of the histidine tagged scFv to coat the plates has been found to result in more of the protein retaining its antigen binding capacity. Plates were washed×3 with PBS, blocked for 2 hrs at 37° C. with 3% BSA in PBS and washed×3 in PBS. Test serum was added (diluted 1:100 or 1:1000 in PBS/3% BSA) and incubated for one hour at room temperature. Plates were washed×3 in PBS and incubated for one hour at room temperature with a second layer HRP-conjugated polyclonal goat anti-mouse Pc antibody at 1:1000 dilution (Sigma, cat. no. A0168). Plates were washed×4 in PBS, developed with ABTS and the A405 nm measured after 30 minutes using a Thermomax™ microplate reader (Molecular devices, Menlo Park, USA).

Results

Immune Response to Protein Vaccine

It was first sought to establish whether mice could mount an effective anti-idiotypic humoral immune response when challenged with a scFv murine antibody in CFA. Six mice were challenged subcutaneously with 25 mg of the B1.8 anti-NIP scFv in CFA, with booster doses two and four weeks later. Ten days after the final challenge, serum from these animals contained insufficient anti-B1.8 antibody to give a positive ELISA signal at 1:100 dilution of the serum.

Immune Response to DNA Vaccine

Plasmid pNIPenv (FIG. 3, see materials and methods for details of construction) encodes a chimeric fusion protein consisting of the ecotropic MoMLV envelope polypeptide Pr80env with a scFv anti-NIP antibody fragment (Kd 4×10⁻⁵ M) inserted 6 aminoacids from the N-terminus. The 33 aminoacid MoMLV env leader sequence is retained, without disruption of the leader cleavage site. As well as the 6 N-terminal amino-acids from the MoMLV envelope protein the scFv also has a further 6 amino-acids derived from the pelB leader remaining at the N-terminus. Expression is driven from promoter/enhancer sequences in the 540 MoMLV long terminal repeat (LTR). Polyadenylation signal sequences are provided by the 3' MoMLV LTR. When transfected into mouse fibroblasts (described above), it was found that pNIPenv gave stable cell-surface expression of functional B1.8 scFv in fusion with the MoMLVenv protein.

Mice were primed via the subcutaneous (three mice) or intramuscular (three mice) route with 16 mg of pSVNIPenv in 200 mM NaCl, with booster doses one and two weeks later. Control mice were vaccinated pSVBCIenv. Pre-vaccination, pre-booster and one week post-vaccination serum samples were tested by ELISA for a humoral response to B1.8scFv. Prior to the second booster, anti-B1.8 scFv antibodies were detected at 1:100 dilution of the serum in three of the six pSVNIPenv-vaccinated mice, two inoculated im and one sc. One week after the second booster, all six mice had easily detectable anti-B1.8 scFv antibodies which did not crossreact with the D1.3 scFv. Sera from control pBCLenv-vaccinated mice remained negative in the anti-B1.8 ELISA.

Anamnestic Response to Protein Vaccine after DNA Vaccine

After 8 weeks, anti-B1.8 antibody titres had fallen in the pSVNIPenv immunised mice. At this point the three mice, originally inoculated intramuscularly with pNIPenv, were challenged intravenously with 20 mg purified B1.8 scFv protein in PBS. Five days later, serum from these mice contained a greatly increased titre of anti-B1.8 antibodies—the average rise was 12 fold and all had antibodies clearly detectable at 1:1000 dilution.

Boosting with Soluble scFv Expression Vector (pNIPstop)

To test whether boosting with a soluble protein expression vector would also boost the antibody titre, mice were inoculated with pNIPstop. Ten weeks after the primary immunisation, the three mice immunised subcutaneously with pNIPenv were inoculated with 8 mg sc and 8 mg im in 200 mM NaCl. Five days after boosting, test bleeds were obtained and assayed for antibody activity. The serum titre increased an average of 10 fold and again all were now positive at 1:1000 dilution.

Comparison of Soluble pNIPstop and pNIPenv in Generating Primary Immune Response To demonstrate the importance of the fusion protein to enhance the immune response we carried out a control experiment to compare the efficacy of two vectors at stimulating a primary immune response. Two groups each consisting of two BALB/c mice were used as before. Serum was obtained by tail bleed as before and then the mice were inoculated weekly×3 with the appropriate plasmid. Twenty-eight days after the start of immunisation serum was again obtained following tail bleeds and assayed for anti-B1.8 activity. 2/2 from the group inoculated with the pNIPenv plasmid were positive at 1:100 dilution and 2/2 in the pNIPstop group were positive. Clearly the env tag is not necessary to stimulate an immune response.

Confirmation that Immune Response Recognises the Native Antigen

A group of five mice immunised four times with DNA (pSV2-BCL1) encoding the unfused BCL1 scFv fragment also generated humoral responses to the idiotype, as detected by binding to the BCL1 fragment in an ELISA (not shown). Moreover, as a clear demonstration of their ability to recognise native antigen in the form required for therapy, these anti-idiotype antisera were shown by FACS analysis to bind to lymphoma cells bearing surface BCL1 Ig. BCL1 cells were pre incubated with serum at a 1:20 dilution before staining with FITC conjugated anti-mouse IgG (Sigma) and followed by FACS analysis. Indeed the immune response was comparable to that for the BCL1 IgM antibody in CFA (FIG. 11). This was in contrast to antisera derived from mice immunised with pSV2-B1.8 which bound only weakly to the BCL1 lymphoma (FIG. 11).

Example 3

Construction of a Vector Suitable for use in Human Recipients

Vector Construction

The initial vectors used in example 2 above were based on Moloney Murine Leukaemia virus vectors and contained large stretches of unmodified viral sequences (Russell et al., 1993 Nucl. Acids Res. 21, 1081–1085). These vectors were shown to be effective in raising anti-idiotype responses and gave no untoward effects in the mice inoculated. Although there is no evidence of danger to man from such vectors it was decided to modify the vectors to avoid any potential risks. There was some concern about two features of the original vectors: the retroviral envelope gene (as it could theoretically be recombined into another retrovirus thus changing its tropism) and the packaging signal (which might allow packaging of the injected DNA into existing human retroviruses). Whilst changing the vector it was decided to incorporate changes which improve the vectors for use in man:—the promoter used to drive expression of the idiotypic scFv was changed to the Rous Sarcoma Virus (RSV) promoter as that has been shown to give expression when directly injected into non-human primate muscle (Jiao et al., 1992 Hum. Gene Ther. 3, 21–33). The present inventors also used a vector which contains a bacterial single strand origin of replication to allow the production of ssDNA which will facilitate sequencing the scFv portion (which is specific for that individual patient) of the vector before injecting into the patient. The vector used is based on a commercially available vector pRc/RSV (British Biotechnology/Invitrogen).

To convert this vector backbone into a vector suitable for genetic immunisation it was desirable to introduce leader sequences, termination signals and to allow for the production of fusion proteins. Fusion proteins do not appear to be necessary for the production of anti-idiotype responses but one way of enhancing the immune response might be to attach suitable proteins—perhaps foreign proteins or perhaps cytokines (Tao & Levy, 1993 Nature 362, 755–758). As fusion proteins were not necessary in animal models the initial human trial will use only a short peptide tag but this is one area for potential future modifications to the protocol.

The vector pSfi/Not.Tag1 was modified to replace the pe1B leader with the human immunoglobulin VH1 leader sequence which permits the encoding of an Sfi I cloning site without modification of the amino-acid sequence. This was introduced with oligonucleotides using the HindIII/Psi I cloning sites and confirmed by sequencing.

This was then cloned as an EcoRI/Blunt—HindIII fragment into the Not I/Blunt—HindIII cut vector pRc/RSV to give the sequence (Seq ID No. 56) between the HindIII/XbaI sites as shown in FIG. 5. The scFv for an individual patient can be inserted at the sites shown by the symbol Λ.

The vector was then tested in two ways:

(i) The scFv B1.8 was cloned into the vector and then the resultant constructed transfected into two cell lines—NSO (a myeloma cell line) and NlH 3T3 (a fibroblast cell line). Utilising the neomycin resistance gene in pRc/RSV stable transfectants were isolated and the supernatant assayed for scFv B1.8 antigen binding activity. In both cases the antibody fragment was expressed and bound to the hapten NIP—the antigen recognised by the monoclonal antibody B1.8. Clones were isolated from the NSO transfected cells and shown to produce 1–3 mg/L of functional scFv in spent culture supernatant.

Figure 6:
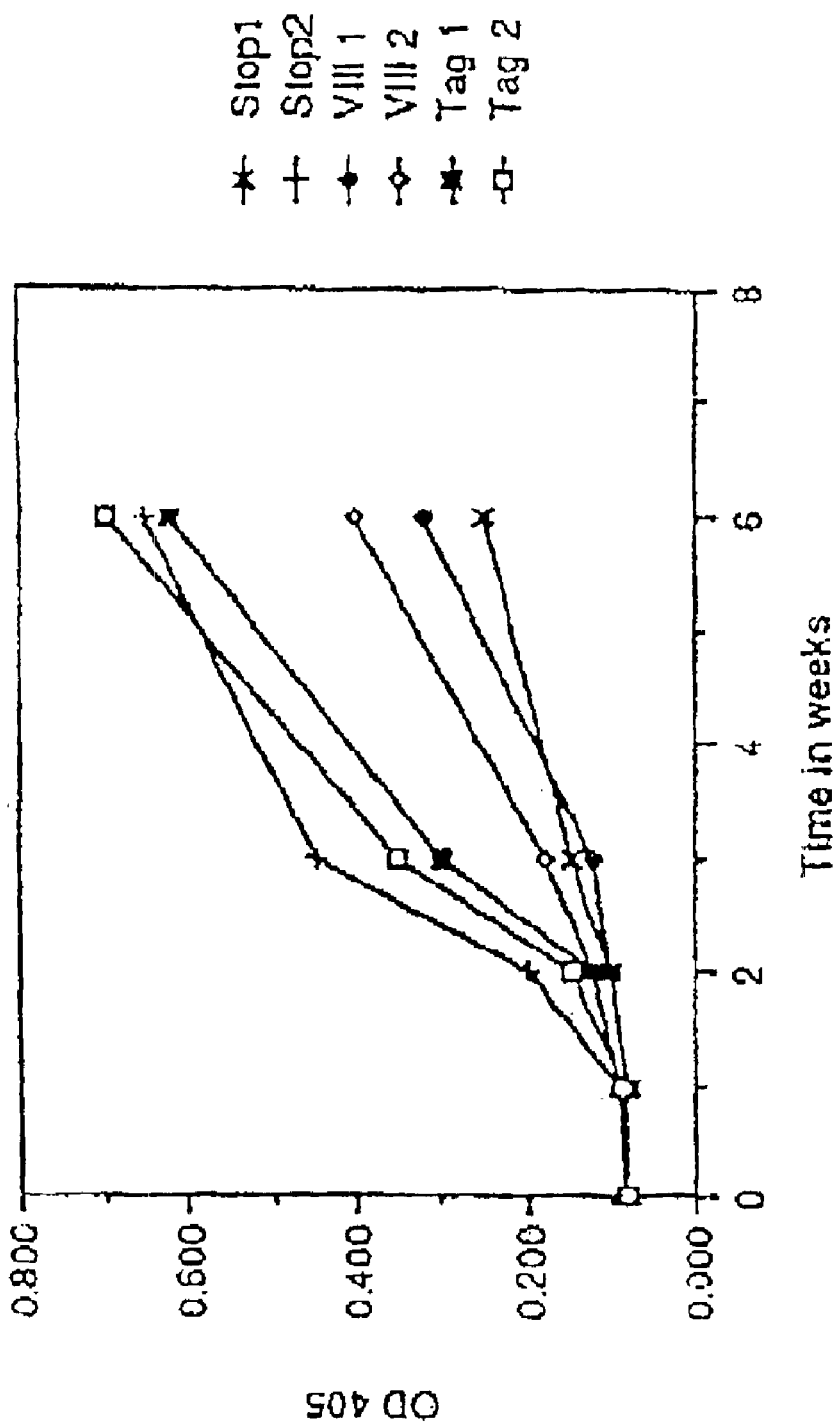
FIG. 6 is a graph showing the results of an immunisation experiment described in example 3.

(ii) The plasmid was used in a genetic immunisation experiment and compared to pSV2-B1.8. They gave comparable results and appear to be superior to a further vector which encodes the Fd bacteriophage gene 8 protein between the Not I and Xba I site (FIG. 6). The likely explanation is that in transfection experiments the level of expression was 10–100 fold lower for the scFv B1.8-Gene 8 fusion. Other investigators have found a strong correlation of level of expression and immune response when using genetic immunisation to raise immune responses to viral proteins (G Rhodes, personal communication).

FIG. 6 (Immunisation of mice with vectors utilising the RSV promoter) shows the results of idiotypic immunisation against the scFv B1.8. The response for individual mice as determined by ELISA at 1:100 serum dilution are shown.

The mice were immunised intra muscularly at weeks 0, 1, 2. Note one mouse with the stop vector (pSV2—B1.8) had a poor response and the response of mice immunised with the gene 8 fusion vector were poor (VIII 1 and VIII2) whereas both those with the peptide tag vector gave good responses (Tag1 and Tag2).

Figure 8:
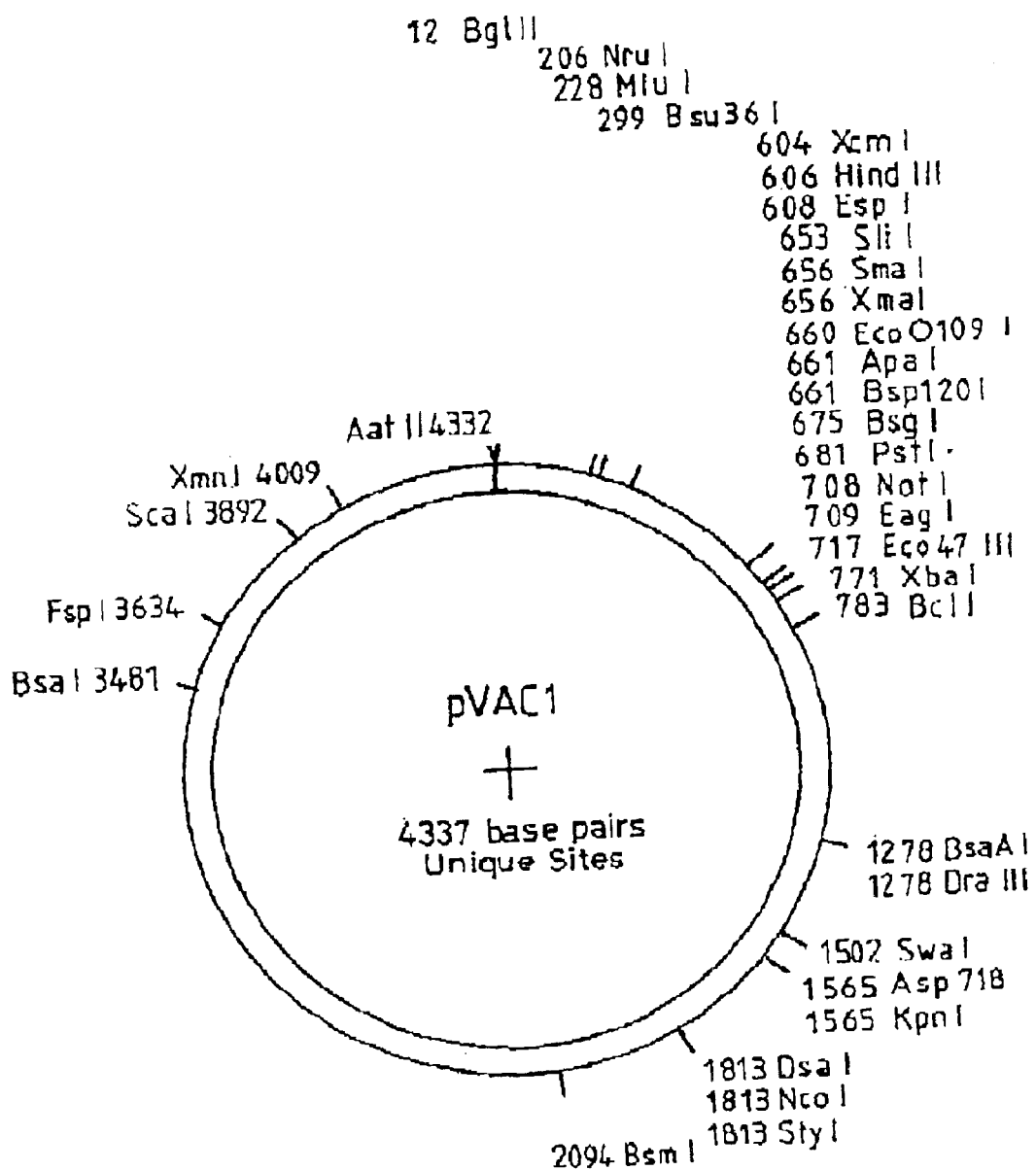
FIG. 8 shows a pVAC1 restriction map.

The sequence (Seq ID No. 58) of the final vector pVAC1 is given in FIG. 7 together with a map of the unique restriction sites (FIG. 8). The sequence in lower case letters in FIG. 7 corresponds to the sequence shown in FIG. 5 through to the two stop codons. The vector pVAC1 is available from the present inventors (at the Cambridge Centre for Protein Engineering, Cambridge, United Kingdom).

Figure 9:
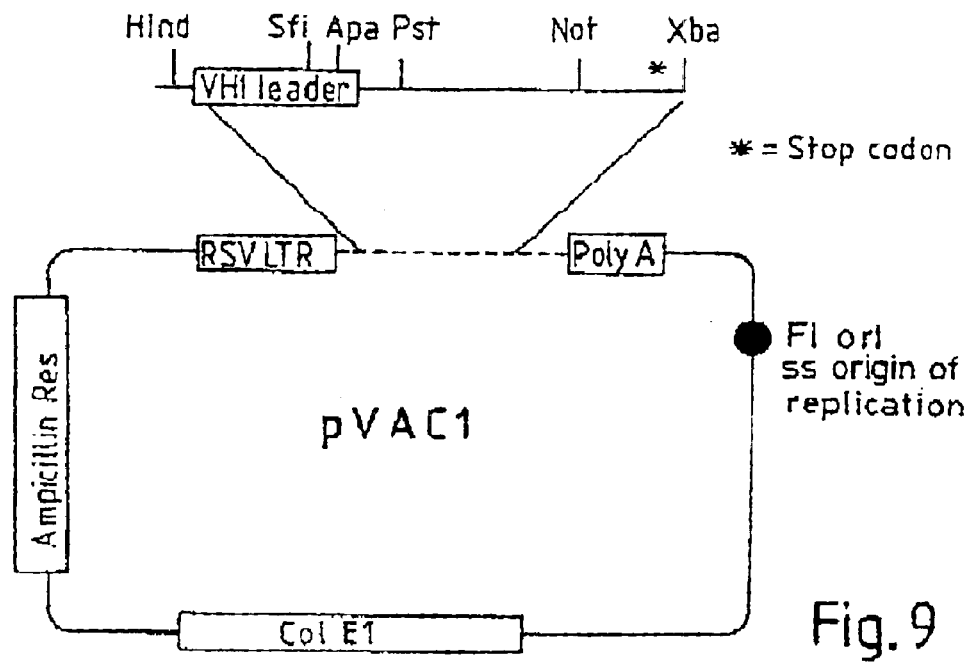
FIG. 9 shows a schematic representation of the main features of pVAC1.

FIG. 9 shows a diagrammatic representation of the vector pVAC1 indicating important restriction sites and important genes.

Figure 10:
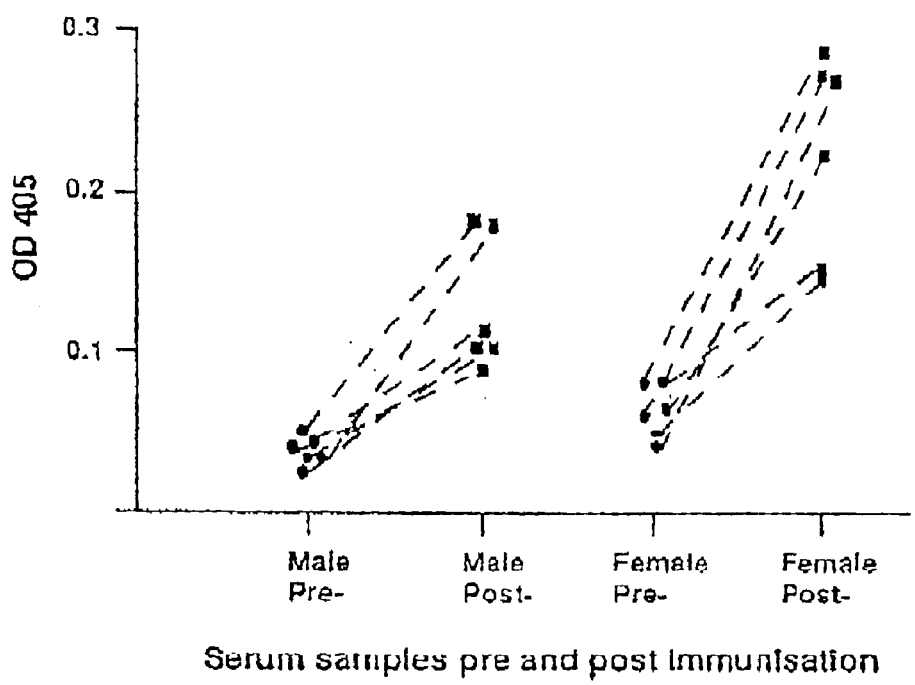
FIG. 10 is a graph showing the results of an immunisation experiment described in example 3.

FIG. 10 is a graph of O.D. (405 nm) against time for male and female mice immunised (by direct injection of DNA) with the pVAC vector expressing B1.8scfv (pVAC1.B1.8). The graph shows that, for individual mice, there was a clear increase in titre following immunisation.

Although the neomycin resistance gene is useful for in vitro testing it is unnecessary for human immunisation. The SV40 promoter used to drive the neomycin resistance gene is also associated with the same risks as other strong promoters. The plasmid to be used for human trials thus has the neomycin gene deleted by an SfiI/Bst BI digest and then blunt ligation. This prevents any such risk.

Discussion of Examples 1–3

The present inventors have demonstrated that a plasmid vaccine encoding a single chain murine antibody/retroviral envelope fusion protein induces a strong humoral immune response to the antibody moiety in BALB/c mice, whereas vaccination with the purified scFv protein, mixed with Complete Freunds Adjuvant gives no detectable response. Induction of B-cell memory appears to occur as boosting with either soluble protein or a soluble scFv expression vector was effective at producing a rapid rise in antibody titre.

The humoral anti-B1.8 response to the plasmid vaccine pNIPenv was clearly superior to that raised against purified B1.8 scFv protein mixed with Complete Freunds Adjuvant. The approach disclosed herein has several advantages. Following gene transfer, there is likely to be a continuous supply of the target antigen, diminishing over a period of days or weeks, whereas injected protein may have a very short half-life. This prolonged exposure to newly synthesised antigen may be important for an optimal immune response and this argument has been used to explain the superiority of live compared to killed viral vaccines.

Antigen-specific T helper cells can amplify both humoral and cellular immune responses by direct cell interaction and by providing appropriate stimulatory cytokines. Several mechanisms can be envisaged whereby the plasmid vaccine may recruit helper T cells more efficiently.

Regardless of the mechanisms involved, the vaccination strategy employed in this study gave a strong humoral immune response to a weakly immunogenic single chain antibody fragment and was superior to vaccination with purified protein plus adjuvant. The scFv gene used in this study could be replaced with a variety of genes or gene fragments encoding other weakly immunogenic idiotypic determinants.

Episomal vectors such as those based on EBV or papova virus may have advantages over current vectors. These should allow high copy number episomal replication and may be more effective. New vectors utilising the pVAC1 HindIII/XbaI insert have been constructed with the expression plasmid pCEP4 (Invitrogen) which contains the EBV origin of replication and EBNA. These have given enhanced levels of expression and greater stability of expression in cell culture experiments using the human osteosarcoma line 791T and may be more efficient in vivo although they also raise new safety issues for human use. More efficient methods of transfection such as liposome mediated and receptor mediated delivery may also improve the efficiency of the process.

Example 4

Initial attempts to induce anti-idiotypic antibodies using DNA scFv vaccines in mouse models, along the lines described above, were encouraging (Stevenson et al, 1995 Immunological Reviews 145:211), and have led to a small safety trial in patients, and the addition of cytokine vectors improved responses even further (Stevenson et al, 1995 cited above), but they still were insufficient to be certain of success in patients possibly having a weakened immune system as a result of their illness and of the conventional therapy. Also, there remains the possibility that tolerance to idiotype may exist in the CD4+T cell population (Bogen, 1996, Eur. J. Immunol. 26:2671).

Tetanus Toxoid (TT) has been used as an carrier protein for inducing immune responses against peptides (Herrington et al. 1992 J. Immunol. 149:717). There is considerable information available on immune responses against TT and the epitopes recognized by human CD4+T cells (Valmori et al, 1992 J. Immunol. 149:717), as well as the mechanisms involved in enhancing immunity to added peptides (Panina-Bordignon et al, 1989 Eur. J. Immunol. 19:2237; Kumar 1992 J. Immunol. 148:1499). Fragment C (FrC), the 50 KD carboxy-terminal portion of the heavy chain of TT, has been found to induce protective immunity against TT which is largely antibody-mediated (Anderson et al. 1996. Infect. and Immun. 64:3168). Importantly, protection could be induced by a DNA vaccine encoding Fragment C (Anderson et al, 1996 Infect. and Immun. 64:3168). The present inventors have attempted to harness these to improve responses to human scFv. Because antibody is known mediator of protection against lymphoma (George et al, J. Immunol. 138:628; Kaminski et al, 1987 J. Immunol. 138:1289), a major question to be addressed was the conformational quality of scFv molecules when fused to FrC.

In the present example, by fusing the gene for Fragment C of Tetanus Toxin to the C-terminus of human scFv, the inventors have promoted the anti-scFv antibody response in mice by >50 fold in 3/3 cases. The induced antibodies are mainly against idiotypic determinants, and react specifically with patients' tumor cells, indicating optimal folding of the scFv molecule in the fusion protein. For both antigenic components of the DNA vaccine, the IgG subclass distribution showed an relative increase in IgG2a as compared with vaccination with IgM protein in adjuvant. In patients, the fusion gene should both promote anti-idiotypic antibody and induce antibodies against Fragment C of Tetanus Toxin. The latter response would provide a potentially useful comparative measure of the ability of patients to respond to conventional antigen delivered via DNA.

MATERIALS AND METHODS

Patients' Tumor Cells and Idiotypic IgM Preparation

Permission to investigate material from patients YJ, CW and WE was obtained from the local Ethical Committee. Patients YJ and CW both had low grade B-cell tumors with high numbers of IgMλ-expressing tumor cells in the blood (81% and 94% of lymphocytes respectively. Blood mononucleocytes (MNCs) were prepared by centrifugation on Lymphoprep (Nycomed, Norway). For preparing idiotypic IgM, heterohybridomas were established by fusion of tumor cells with the mouse plasmacytoma cell line OURI, an ouabain-resistant subclone of the X-63-Ag8.653 line, as described by Pascual et al (1992 J. Immunol. 149:2337). Hybridomas were cloned and selected for IgMλ secretion by ELISA (Pascual et al, cited above), and IgM was purified from the supernatants of expanded clones by immunosorption using Sepharose 4B coupled to sheep anti-human μ antibody. Patient WE had a B-cell tumor associated with cold agglutinin disease; in this case, a hybridoma secreting an IgMx anti-red cell antibody with specificity for the I/i antigen was established from tumor cells. This hybridoma has been described previously, and has the designation FS-6 in a previous study of anti-I/i MoAbs (Pascual et al, cited above).

Amplification and Sequencing of V-genes and FrC Genes

Preparation of cDNA from blood MNCs or hybridoma cells was as described previously (Hawkins et al, 1994 Blood 83:3279). To identify tumor-derived $V_H$ and $V_L$ genes, PCR amplification was carried out using a mixture of 5'-oligonucleotide primers specific for each of the $V_H$ leader sequences of the $V_H$1–6 families, together with a mixture of 3' primers specific for the $J_H$ sequences (Hawkins et al, 1994 Blood 83:3279). A similar procedure was applied for $V_L$, using 5'-primer mixes specific for framework regions of either Vκ or Vλ with 3'-primer mixes specific for $J_L$, according to the light chain type (Hawkins et al, 1994 cited above). Following cloning and sequencing, predominant repeated identical sequences were seen in all cases. The FrC sequence was amplified using pTech2 (kindly provided by Medeva plc, Leatherhead, Surrey, UK) as template (Khan et al, 1994 J. Immunol. 153:5634).

Assembly and Plasmid Purification

Tumour-derived $V_H$ and $V_L$ genes were assembled as scFv by a two-step procedure as described previously by Hawkins et al (1994 Blood 83:3279). The scFv-FrC fusion constructs were made by a similar two-step assembly process, using the primers shown in Table 3 (Seq ID No.s 67–73). In the first step, scFv and FrC were amplified separately using the paired primers for adding a 3' linker to scFv and a 5' primer to FrC. PCR was performed in a final volume of 50 μl with 0.1 μg of DNA template, 20 pmol of each primer, 50 μmol of dNTPs and 2.5 units of Pfu DNA polymerase with reaction buffer (Stratagene, La Jolla, Calif.).

Amplification consisted of an initial denaturation step of 5 min at 94° C., then 5 cycles of 94° C. for 30 seconds, 42° C. for 30 seconds, and 72° C. for 3 min, followed by 20 cycles of 94° C. for 30 seconds, 60° C. for 30 seconds and 72° C. for 3 min. The PCR products were analyzed on a 1.2% agarose gel, recovered using GENECLEAN II Kit (Bio101, Vista, Calif.) and eluted in 25 μl of water. In the second step, 5 μl of each PCR product was combined and assembled by PCR using the $V_n$ scFv assembly primer and the FrC anti-sense primer only. PCR conditions were as above except with an extension step of 5 min. A 5' SfiI restriction site was introduced by scFv assembly primer and a NotI site was introduced by the FrC anti-sense primer. The full-length scFv-FrC product was gel-purified, digested with SfiI and NotI and cloned into the pRSV vector (based on pUC 119, see Hawkins & Winter 1992 Eur. J. Immunol. 22, 867, and previous examples). The scFv FrC constructs were then cloned into the pcDNA3 vector (available from Invitrogen, San Diego, Calif.) as a HindIII-NotI fragment.

Vaccination Protocol

BALB/c mice were immunized with 50 μg of DNA in normal saline injected into two sites in the quadriceps muscles. Injections were at day 0, 21 and 42, and tail bleeds were taken at days 20 and 41, with a final terminal bleed at day 63. Immunization with IgM from patient YJ was carried out using Complete Freund's adjuvant (CFA), with subcutaneous injections of 50 μg at days 0, 21 and 28, followed by a terminal bleed at day 47.

Measurement of Antibody Responses

Antibody against FrC was measured by ELISA using recombinant FrC kindly provided by Dr. Stephen Chatfield (Medeva plc, Imperial College, London), coated to microtitre wells at 1 μg/ml. Dilutions of sera were made in PBS containing Tween 20 (0.1%) and BSA (0.1%), and detection of bound mouse 1gG was with HRP-sheep anti-mouse Fcγ (Serotec, Kidlington, UK). A pooled terminal serum was assigned an arbitrary value of 4000 U/ml to act as a comparative standard. Antibody against patients' tumor-derived IgM was measured by ELISA using idiotypic IgM coated to microtitre wells at 0.5 μg/ml. Dilutions of sera were made with PBS-Tween 20 (0.1%) and bound IgG was detected as above. To distinguish between individual IgG subclasses HRP-rabbit anti-mouse IgG1, and HRP-goat anti-mouse IgG2a or IgG2b (Harlan, UK), were used as detecting antibodies.

Reactivity of Antibodies with Tumor Cells

Sera from groups of immunized mice were collected at day 63 and pooled for analysis by FACS-SCAN. Tumour cells from patients were incubated with sera diluted to 1:20 with PBS/azide, and bound antibodies were detected with FITC-sheep anti-mouse IgG.

Results $V_H$ and $V_L$ Sequences of Patients' Tumors

Figure 12:
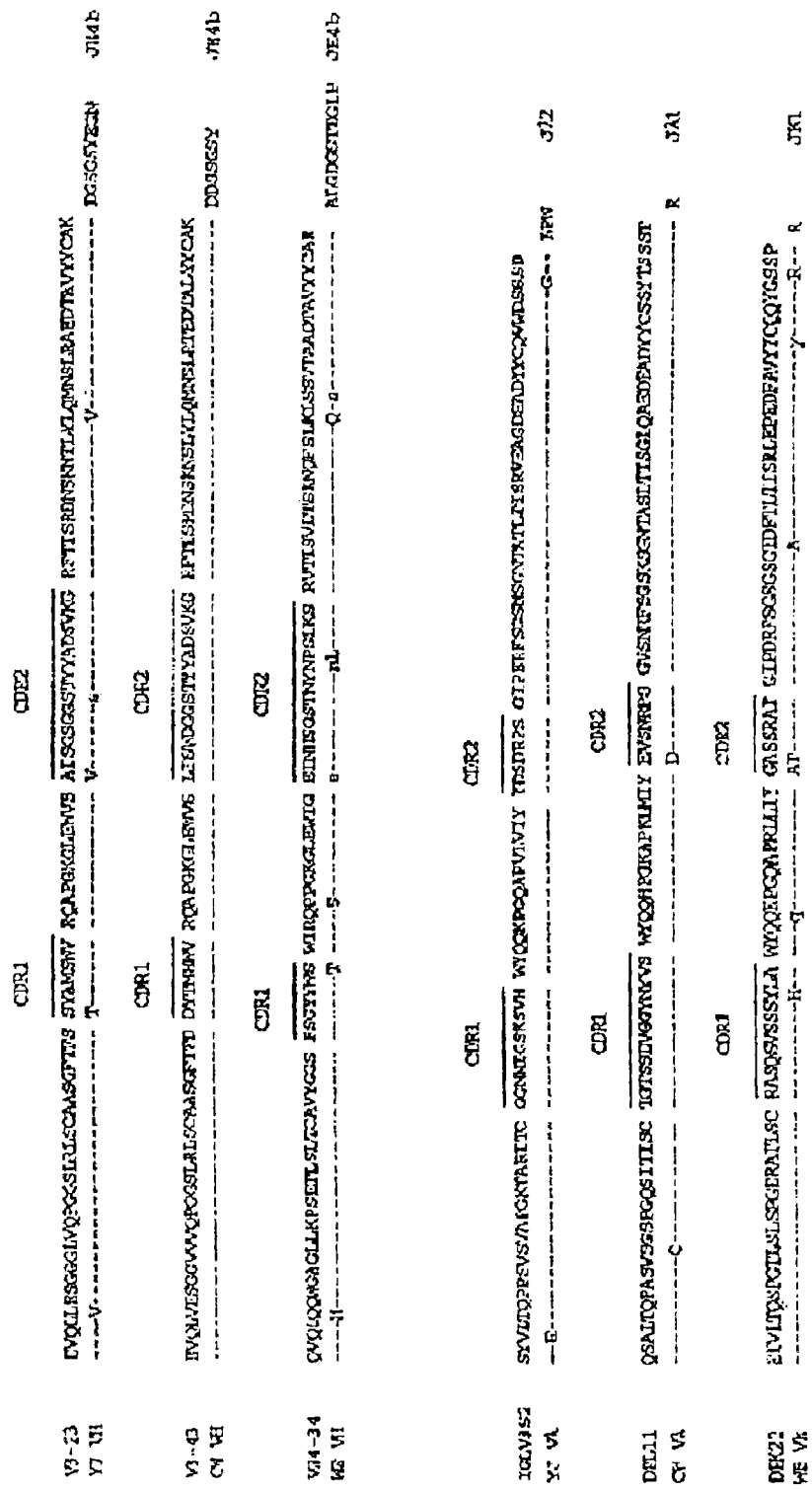
FIG. 12 shows the deduced amino acid sequences of $V_H$ and $V_L$ genes from patients YJ, CW and WE, described in example 4 (SEQ ID NOS: 74–79)

For patients YJ and CW, cloning and sequencing of the PCR products obtained using mixed $V_H$ and $V_L$ 5' primers in combination with the appropriate 3'J primer sequences (Table 3) produced clear predominant sequences. For YJ, 4/4 identical $V_H$3 ($V_{3-23}$) sequences and 5/5 Vλ (1GLV3S2) were identified, and for CW, 9/9 identical $V_H$ 3 ($V_{3-43}$) sequences and 6/6 Vλ (DPL11) were obtained (see FIG. 12). In each case, the repeated sequences of $V_H$ had identical CDR3 "clonal signatures", and no additional sequences from normal B cells seen, reflecting the predominance of tumor cells in the blood samples. The hybridomas established from tumor cells were also investigated by PCR/sequencing and were found to have the same $V_H$ and $V_L$ sequences as the predominant PCR products from whole blood. Derivation of the hybridoma from tumor cells of patient WE (PS-6) has been described previously (Pascual et al, 1992 J. Immunol. 149:2337). The tumour-derived $V_H$ and $V_L$ sequences used to assemble scFv are shown in FIG. 12 (Seq ID No.s 74–80). In FIG. 12, the $V_H$ (upper three sequences) and $V_L$ (lower three sequences) are compared with the closest germ line gene—only the sequence differences are shown for the patients' scFv. Amino acid substitution mutations are shown in Upper case letters, silent mutations are shown in lower case.

Antibody Response Against FrC

The performance of the DNA vaccine containing the gene encoding FrC of TT alone was first tested, with serum antibody against FrC protein ($log_{10}$ units per ml) against time (days) as the read-out. The results are shown in panels 1–6 in FIG. 13. Panels 1 and 2 are for the leaderless FrC sequence, panels 3 and 4 show results for the FrC sequence with leader, panel 5 shows the results for scFv-only sequences from patients YJ (left) and CW (right), and panel 6 shows the results for scFv-FrC fusion sequences from patients YJ (left) and CW (right). The horizontal dotted line indicates the background level of the ELISA.

Figure 13:
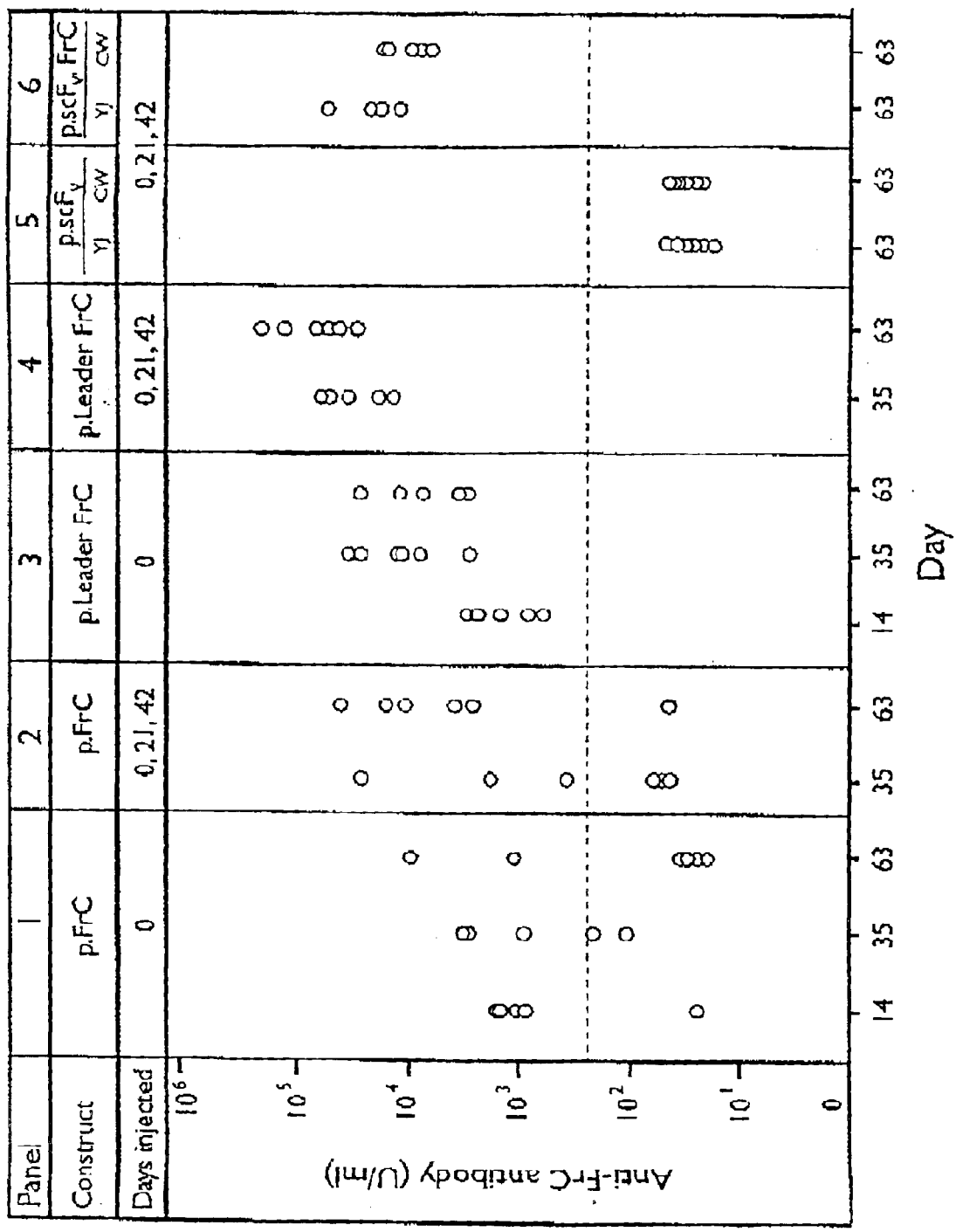
FIGS. 13 and 14 show the results of an immunisation experiment described to example 4.

Following intramuscular injection of a single dose of 50 μg of plasmid at day 0, antibody was detectable at significant levels (>400 U/ml) in ⅗ mice at day 35, and was still evident in two of these at day 63 (FIG. 13, panel 1). Background levels of antibody induced by the control plasmid (containing scFvYJ or scFvCW only) were consistently <400 U/ml (panel 5). Boosts of the same dose of DNA vaccine at days 21 and 42 improved titers with levels of >2000 U/ml in ⅚ mice at day 63 (panel 2). The role of a human $V_H1$ leader sequence which would take the protein into the endoplasmic reticulum was also investigated using FrC alone. As shown in panel 3 (FIG. 13), this appeared to improve antibody responses, with even a single dose inducing high levels. Boosts then were able to increase the levels to >20,000 U/ml in all mice (panel 4). The scFv FrC plasmid has the same leader sequence, but encodes a large fusion protein (~80 KD) which may affect expression. Levels of anti-FrC antibody induced by the p.scFvYJ.FrC or p.scFvCW.FrC fusion constructs were high (panel 6), although possibly slightly reduced when compared with p.FrC alone (panel 4, day 63).

Antibody Response Against scFv-FrC Fusion Proteins

Figure 14:
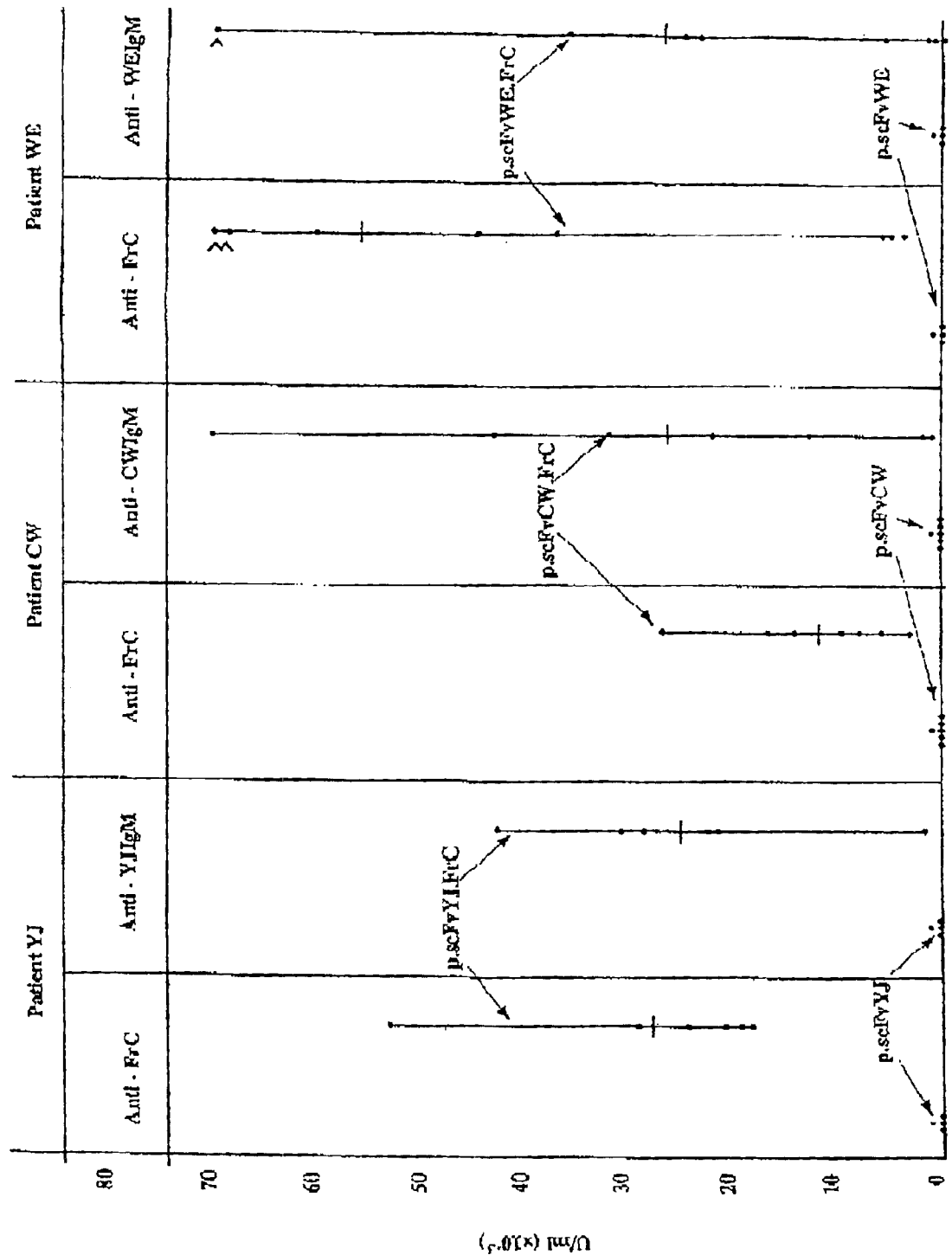

The ability of the three scFv.FrC fusion constructs to induce anti-FrC antibodies is shown in FIG. 14. Each DNA vaccine contained the genes encoding scFv either alone (p.scFv), or fused to FrC of TT (p.scFv.FrC), with scFv sequences derived from patients YJ, CW or WE as indicated. Injections of DNA (50 μg) were at days 0, 21 and 42; blood samples were taken at day 63 for YJ and CW, and day 42 for WE. Antibodies against FrC or against patient-derived IgM were measured by ELISA. For DNA vaccines containing only scFv sequences, antibody responses against FrC or IgM were insignificant.

Following the same protocol as for the construct containing FrC only, specific anti-FrC antibodies were induced in all mice; levels at day 63 are shown for scFvYJ.FrC and scFvCW.FrC constructs, and levels at day 42 shown for the scFvWE.FrC construct. In each case, the constructs with scFv alone failed to induce significant levels of antibody against FrC, as expected. However, constructs with scFv alone also failed to induce significant antibody against the patients' tumor-derived IgM proteins. In contrast, the scFv-FrC fusion constructs induced high levels of antibody against the patient's IgM in all three cases, with mean values increased ~x50 fold. In the majority of the mice, antibodies were detectable at day 21 after a single dose of vaccine (data not shown), and responses were increased after the boosts, with all mice responding by day 42 or 63 (FIG. 14).

Specificity of Anti-scFv Antibodies

Figure 15:
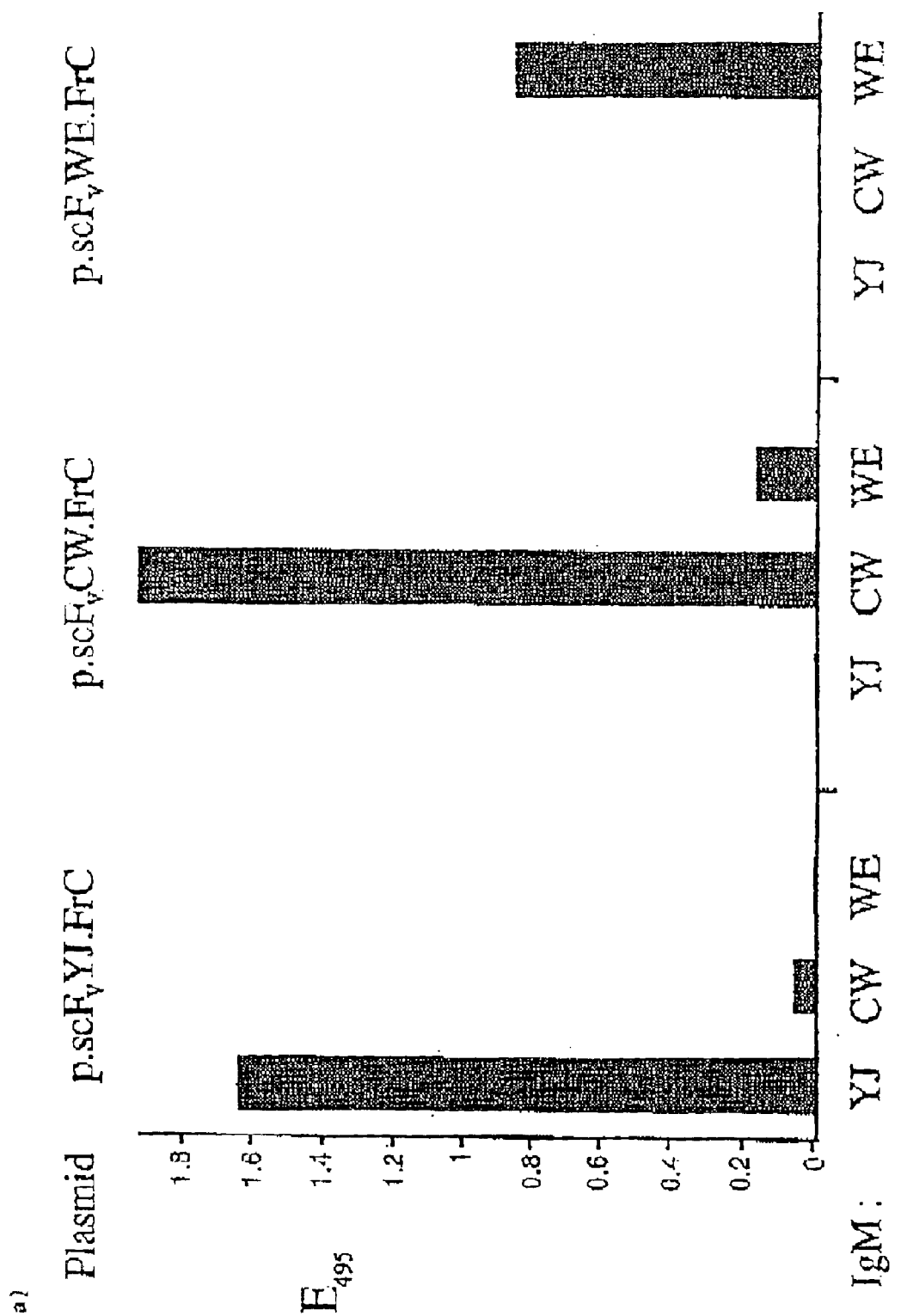
FIGS. 15, 16 and 17 are further graphs showing the results of immunisation experiments described in example 4.

Antisera from day 42 or day 63 bleeds were pooled from each vaccinated group and tested for binding to the other monoclonal IgM preparations, with results shown in FIG 15. In the figure, sera from mice vaccinated with the DNA fusion constructs (indicated at the top of the charts) containing scFv from the three different patients were tested for reactivity with IgM from each patient's tumor cells by ELISA ($E_{495}$ shown on the left hand side). In each case, reactivity was highly specific for the patient-derived IgM., with no detectable cross-reaction even between the two IgMs derived from IgMλ involving the $V_H3$ family (YJ and CW). These findings suggested that antibodies were directed mainly against personal idiotypic determinants.

Figure 16:
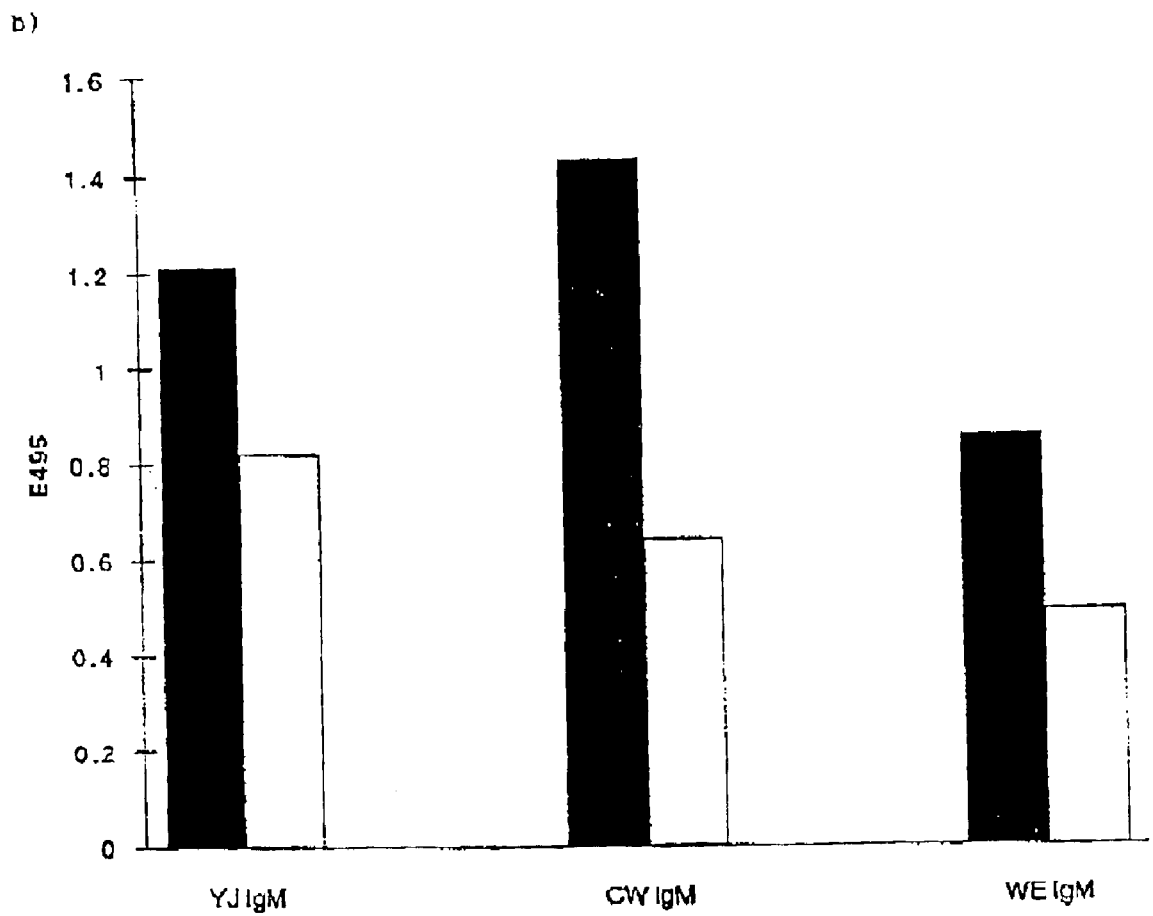

This was tested further by adding normal human serum to the antisera to assess its ability to block reactivity. The dilution of antiserum was chosen to lie below the saturation point (~70% of the plateau level) for maximal sensitivity to inhibition. The results (FIG. 16) indicate that, in each case, normal serum, at 50% final concentration, was only able to partially block binding to the tumor IgM. In FIG. 16, the height of the bars indicates the ELISA result ($E_{495}$) in the presence of serum alone (solid shaded columns) or in the presence of serum plus 50% normal human serum (empty columns). Serum Ig would be expected to display framework regions of a wide range of $V_H$ and $V_L$ gene segments, with the V3 gene used by YJ, $Y_{3-23}$, being particularly commonly used (Cook & Tomlinson 1995 Immunol. Today 16–237). The failure of serum totally to block reactivity therefore supports the conclusion that a significant proportion of the antibodies are directed at personal idiotypic determinants. Clearly, these personal determinants are present in the inducing scFv and are displayed by IgM. Since personal idiotypic determinants are usually conformation dependent (Capra 1977 Fed. Proc. 26:204), this strongly suggests that the scFv in the fusion protein is folded in a manner comparable to the original IgM in all three cases.

Figure 17:
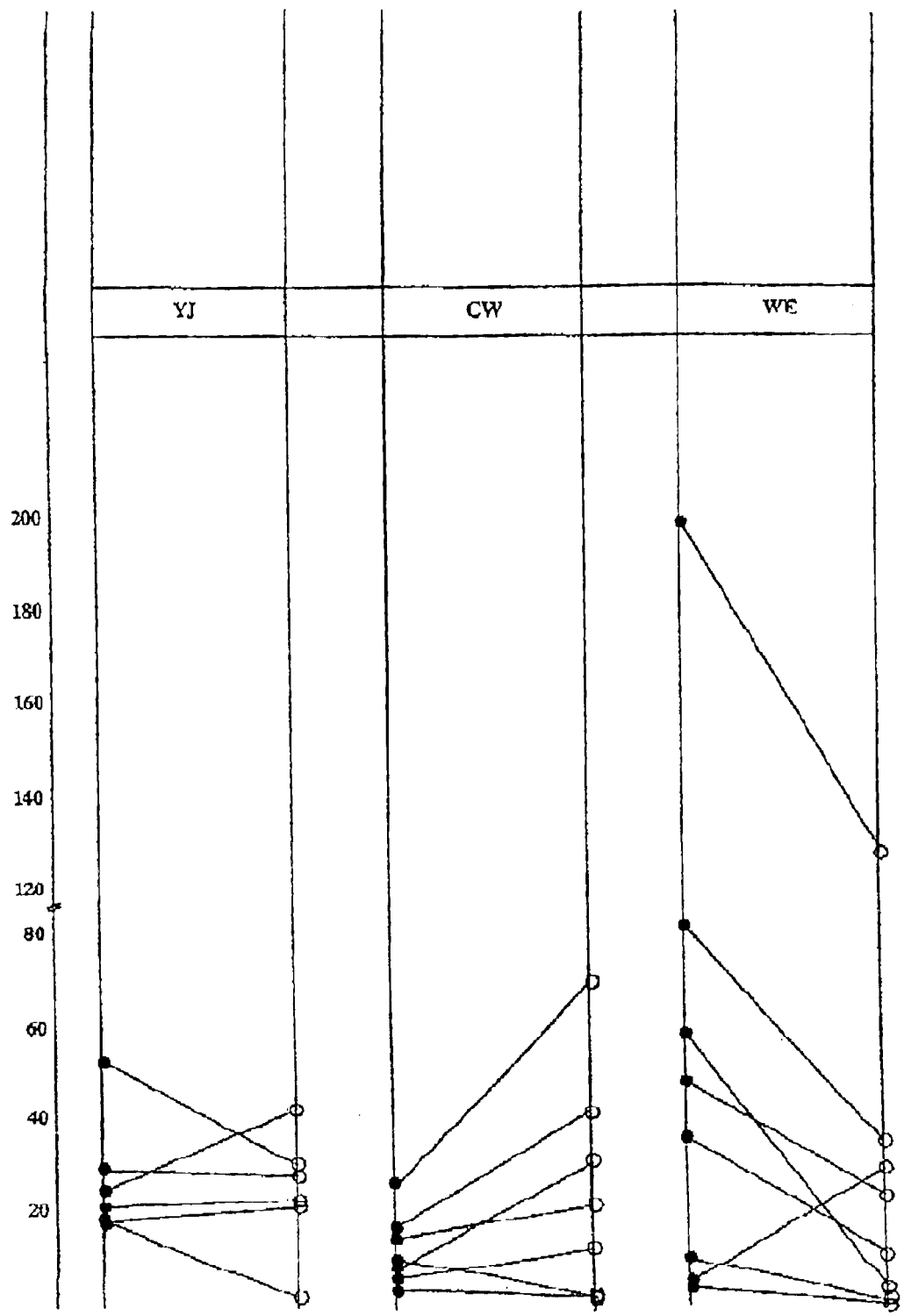

To investigate whether antibodies against the two components of the fusion protein were produced in parallel, individual antisera were tested for levels of anti-FrC or antibodies against the patient's IgM. The results are indicated in FIG. 17. The figure shows the levels of antibodies against either FrC of TT (●) or against tumor-derived IgM (○), induced by DNA vaccines containing scFv-FrC fusion genes from patients YJ, CW or WE, were measured by ELISA (units per ml,×10 $^{-3}$). Sera were from individual mice and were taken at day 63 following injections of DNA vaccines at days 0, 21 and 42.

The results were quite variable for the three patients and, although there was a tendency for comparable responses against the two fused antigens, there was no simple correlation in levels of antibodies against the two components of the fusion protein.

Reactivity of Antisera with Tumor Cells

Figure 18A:
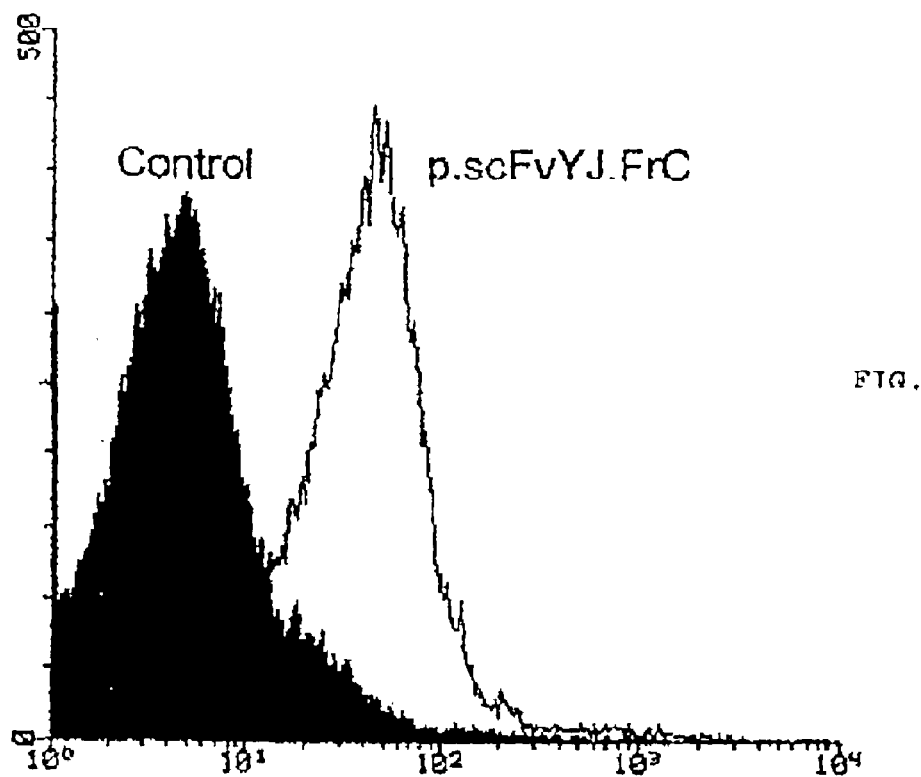
FIGS. 18a and 18b show the reactivity of antibodies with tumour cells, as determined by FACS analysis, as described in example 4.
Figure 18B:
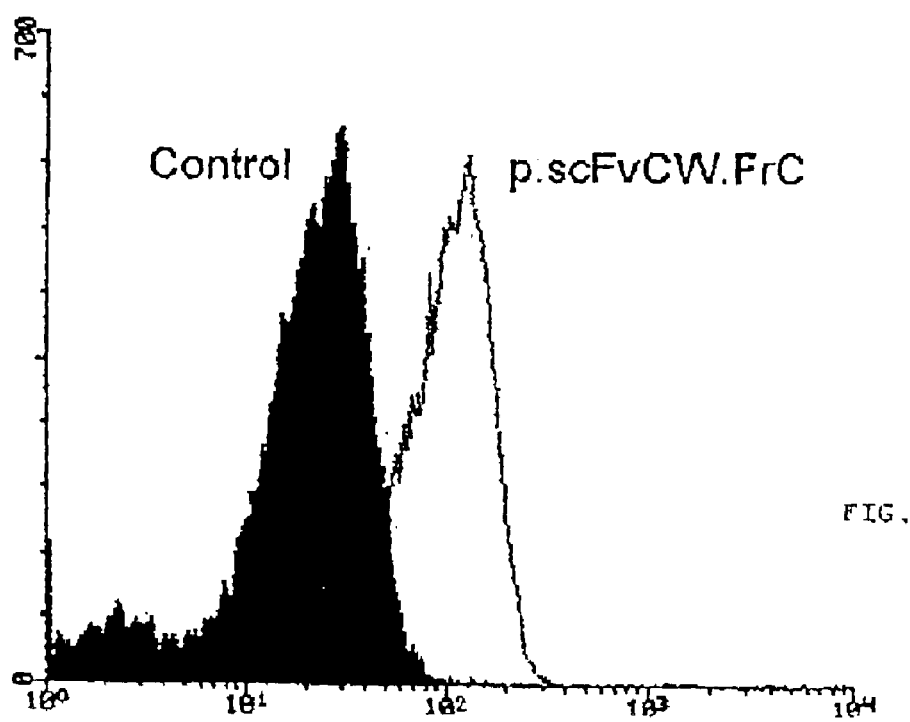

Pooled antisera from the day 63 bleeds were tested for reactivity with tumor cells by immunofluorescence. This was carried out with cells from YJ (FIG. 18A) and CW (FIG. 18B) since no tumor cells were available from WE. The results (FIG 18) show strong and specific binding to tumor cells of the patient from whom the scFv was derived. Serum from mice vaccinated with a control murine scFv FrC construct showed no significant binding. For cells from patient CW, the FITC-sheep anti-mouse IgG detecting antibody showed some background reactivity which was not increased by the control antiserum.

Immunoglobulin Subclasses of Antibodies Against FrC or IgM

The anti-FrC and anti-scFv components of pooled antisera against the three scFv-FrC fusions were assayed for IgG subclasses, IgG1, IgG2a and IgG2b. Results (Table 4) indicate that, for the DNA vaccines, the ratio of IgG1:IgG2a was similar for both antigens, varying from 0.3–1.8:1. In contrast, the antibody response to whole YJIgM protein in CFA was dominated by the IgG1 subclass, with a ratio of IgG1:IgG2a of 11.8:1 (table 4).

Discussion of Example 4

DNA vaccines are being used increasingly to induce immune responses against pathogens (Davis & Whalen 1995 In *Molecular and Cell Biology of Human Gene Therapeutics* Ed. George Dickson. Chapman & Hall p368). Clearly they provide a relatively simple vaccine vehicle, with immense possibilities for manipulation of antigenic sequences. For tumor antigens, a vaccine must operate as a treatment rather than as a prevention, and often in the face of residual disease. Chemotherapy and disease are likely to have damaged the ability of patients to mount an effective immune response. Finally, there is the potential problem of tolerance to tumor antigens. In the case of idiotypic determinants against lymphoma, mouse models have shown that idiotypic IgM protein can induce protective immunity against tumor challenge, largely mediated by anti-idiotypic antibody (George et al, J. Immunol. 138:628; Kaminski et al, 1987 J. Immunol. 138:1289). For protein vaccines, T-cell tolerance can be avoided by coupling idiotype protein to KLH (Kwak et al, 1992 N. Engl. Med 327:1209). However, idiotypic protein is difficult and expensive to prepare, and replacing protein vaccines with DNA would facilitate clinical application.

Our results with DNA vaccines encoding FrC, a non-toxic carboxy-terminal portion of TT, have confirmed previous studies (Anderson et al, 1996. *Infect. and Immun.* 64:3168) in showing its efficacy in inducing anti-FrC antibodies. We have also found that the presence of a leader sequence increases the response. In the fusion constructs, with scFv in the upstream position, antibody responses to FrC remained at a high level, indicating that expression and processing of FrC was not significantly affected by the fused scFv. For scFv from three patients, promotion of antibody responses by fusion to FrC was quite dramatic, with ~×50 fold increases observed. Specificity analysis indicated that a significant proportion of the antibodies was against personal idiotypic determinants. This supports the concepts that scFv can fold into its natural conformation while in fusion with FrC and it has been important to establish this point using a variety of patient's scFv sequences.

Although the antibodies to scFv and FrC did not show a strict correlation in levels, there was the same trend of high or low responsiveness in individual mice. It may be that antibody responses reflect the balance between B cells expressing anti-Ig or anti-FrC, which presumably both present antigen to CD4+T cells specific for FrC. The similar trend however will be helpful in using the anti-FrC response as an index of immune potential. There was also a similar pattern in the IgG subclass profile of the two antibody populations, with the plasmid constructs consistently inducing significant levels of IgG2a indicative of a TH1 response (Abbas et al, 1996 Nature 383:787). This differs from the IgG1-dominated response induced by IgM protein plus adjuvant, and open other possibilities for therapeutic exploitation.

One potential problem in applying this approach to vaccination of patients is that there is likely to be a pre-existing immunity against TT, and that this might cause epitope suppression (Corradin & Watts 1995 Curr. Top. Microbiol. Immunol. 195:77). However, there are promiscuous T-cell epitopes in TT which bind to a wide range of HLA haplotypes, and are recognized by T cells (Valmori et al, 1992 J. Immunol. 149:717; Panina-Bordignon et al 1989 Eur. J. Immunol. 19:3237). A similar promiscuity is seen for various mouse strains (Kumar et al, 1992 J. Immunol. 148–1499). If T-cell help is the limiting factor in generating immunity, it should be possible to design vaccines incorporating only the promiscuous epitopes thereby avoiding epitope suppression. A further bonus for patients is that the immune response against FrC could provide an index of immune status. Clearly, mobilizing pathways designed to attack pathogens may have benefit in fighting tumors.

TABLE 1

```
Primary PCR primers
Human VH Back

HVH1BACK      SEQ ID NO:1     CAG GTG CAG CTG GTG CAG TCT G
HVH2BACK      SEQ ID NO:2     CAG GTC AAC TTA AGG GAG TCT G
HVH3BACK      SEQ ID NO:3     CAG GTG CAG CTG GTG GAG TCT G
HVH4BACK      SEQ ID NO:4     CAG GTG CAG CTG CAG GAG TCG G
HVH5BACK      SEQ ID NO:5     GAG GTG CAG CTG CTG CAG TCT G
HVH6BACK      SEQ ID NO:6     CAG GTA CAG CTG CAG CAG TCA G
Secondary and Assembly primers
Human VH Back HVH1Sf        SEQ ID NO:25    TCG CGG CCC AAC CGG CCA TGG CCC AGG TGC AGC TGG TGC AG
HVH2Sf        SEQ ID NO:26    TCG CGG CCC AAC CGG CCA TGG CCC AGG TCA ACT TAA GGG AG
HVH3Sf        SEQ ID NO:27    TCG CGG CCC AAC CGG CCA TGG CCG AGG TGC ACC TGG TCG AG
HVH4Sf        SEQ ID NO:28    TCG CGG CCC AAC CGG CCA TGG CCC AGG TGC ACC TGC AGG AG
HVH5Sf        SEQ ID NO:29    TCG CGG CCC AAC CCG CCA TGG CCG AGG TGC AGC TGC TGC AG
HVH6Sf        SEQ ID NO:30    TCG CGG CCC AAC CGG CCA TGG CCC AGG TAC AGC TGC AGC AG
Primary PCR primers
Human IH HJ12FOR       SEQ ID NO:7     TGA GGA GAC GGT GAC CAG GGT GCC
HJ45FOR       SEQ ID NO:8     TGA GGA GAC GGT GAC CAG GGT TCC
HJ3FOR        SEQ ID NO:9     TGA AGA GAC GGT GAC CAT TGT CCC
HJ6FOR        SEQ ID NO:10    TGA GGA GAC GGT GAC CGT GGT CCC
Secondary and Assembly primers
Human IH SCHJ12FOR     SEQ ID NO:31    AGA GCC ACC TCC GCC TGA ACC GCC TCC ACC TGA GGA GAC GGT GAC CAG GG
SCHJ45FOR     SEQ ID NO:32    AGA GCC ACC TCC GCC TGA ACC GCC TCC ACC TGA GGA GAC GGT GAC CAG GG
SCHJ3FOR      SEQ ID NO:33    AGA GCC ACC TCC GCC TGA ACC GCC TCC ACC TGA AGA GAC GGT GAC CAT TC
SCHJ6FOR      SEQ ID NO:34    AGA GCC ACC TCC GCC TGA ACC GCC TCC ACC TGA GGA CAC GGT GAC CGT GG
Primary PCR primers
Human KAPPA BACK HK14BACK      SEQ ID NO:11    GAC ATC CAG ATG ACC CAG TCT CC
HK26BACK      SEQ ID NO:12    GAT ATT GTG ATG ACT CAG TCT CC
HK30BACK      SEQ ID NO:13    GAA ATT GTG TTG ACG CAG TCT CC
```

TABLE 1-continued

| | | |
|---|---|---|
| HK50BACK | SEQ ID NO:14 | GAA ACG ACA CTC ACG CAG TCT CC |

Secondary and Assembly primers
Human KAPPA BACK

| | | |
|---|---|---|
| SCK14BACK | SEQ ID NO:35 | GGA GCA GGT GGC TCT GGC GGT GGC GGA TCG GAC ATC CAG ATG ACC CAG |
| SCK26BACK | SEQ ID NO:36 | GGC GGA GGT GGC TCT GGC GGT GGC GGA TCG GAT ATT GTG ATG ACT CAG T |
| SCK30BACK | SEQ ID NO:37 | GGC GGA GGT GGC TCT GGC GGT GGC GGA TCG GAA ATT GTG TTG ACC CAG T |
| SCK50BACK | SEQ ID NO:38 | GGC GGA GGT GGC TCT GGC CGT GGC GGA TCG GAA ACC ACA CTC ACG CAG |

Primary PCR primers
Human J-KAPPA

| | | |
|---|---|---|
| HJK124FOR | SEQ ID NO:15 | ACG TTT GAT CTC CAC CTT GGT CCC |
| HJK30FOR | SEQ ID NO:16 | ACG TTT GAT ATC CAC TTT GGT CCC |
| HJK50FOR | SEQ ID NO:17 | ACG TTT AAT CTC CAG TCG TGT CCC |

Secondary and Assembly primers
Human J-KAPPA

| | | |
|---|---|---|
| HJK124NOT | SEQ ID NO:39 | GAT ATG AGA TAC TGC GGC CGC ACG TTT GAT CTC CAC CTT GG |
| HJK30NOT | SEQ ID NO:40 | GAT ATG AGA TAC TGC GGC CGC ACG TTT GAT ATC CAC TTT GG |
| HJK50NOT | SEQ ID NO:41 | GAT ATG AGA TAC TGC GGC CGC ACG TTT AAT CTC CAG TCG TG |

Primary PCR primers
Human LAMBDA BACK

| | | |
|---|---|---|
| HL10BACK | SEQ ID NO:18 | CAG TCT GTG TTG ACG CAG CCG CCC TC |
| HL20BACK | SEQ ID NO:19 | CAG TCT GCC CTG ACT CAG CCT GCC TC |
| HL30BACK | SEQ ID NO:20 | TCC TAT GAG CTG ACT CAG CCA CVC TC |
| HL40BACK | SEQ ID NO:21 | CAC GTT ATA CTG ACT CAA CCG CCC TC |

Secondary and Assembly primers
Human LAMBDA BACK

| | | |
|---|---|---|
| SCHL1BACK | SEQ ID NO:42 | GGC GGA GGT GGC TCT GGC GGT GGC GGA TCG CAG TCT GTG TTG ACG CAG |
| SCHL2BACK | SEQ ID NO:43 | GGC GGA GGT GGC TCT GGC GGT GGC GGA TCG CAG TCT GCC CTG ACT CAG |
| SCHL3BACK | SEQ ID NO:44 | GGC GGA GGT GGC TCT GGC GGT GGC GGA TCG TCC TAT CAG CTG ACT CAG |
| SCHL4BACK | SEQ ID NO:45 | GGC GGA GGT GGC TCT GGC GGT GGC GGA TCG CAC GTT ATA CTG ACT CAA C |

Primary PCR primers
Human J-LAMBDA

| | | |
|---|---|---|
| HJL1FOR | SEQ ID NO:22 | ACC TAG GAC GGT GAC CTT GGT CCC |
| HJL2FOR | SEQ ID NO:23 | ACC TAG GAC GGT CAG CTT GGT CCC |
| HJL7FOR | SEQ ID NO:24 | ACC GAG GAC GGT CAG CTG GGT GCC |

Secondary and Assembly primers
Human J-LAMBDA

| | | |
|---|---|---|
| HJL10NOT | SEQ ID NO:46 | GAT ATG AGA TAC TGC GGC CGC ACC TAG GAC GGT GAC CTT GG |
| HJL23NOT | SEQ ID NO:47 | GAT ATG AGA TAC TGC GGC CGC ACC TAG GAC GGT CAG CTT GG |
| HJL70NOT | SEQ ID NO:48 | GAT ATG AGA TAC TGC GGC CGC ACC GAG GAC GGT CAG CTG GG |

Notes:
1. The restriction sites underlined in the VHBAK primers are PstI sites and in the JH primers are BstEII.
2. The length of the secondary PCR primers varies to equalise the annealing temperatures.

TABLE 2

RESULTS OF SEQUENCE ANALYSIS FROM PATIENT SPECIMENS.

IDENTICAL SEQUENCES (NUMBER SEQUENCED)

| | VH | Vλ | Vk | % HISTOLOGICAL TUMOUR INVOLVEMENT |
|---|---|---|---|---|
| Controls: | | | | |
| NLN | 0(12) | 0(8) | 0(8) | |
| SPL | 0(10) | 0(10) | 0(10) | |
| Patients: | | | | |
| 1 | 9(16)* | 7(16)* | ND | 60 |
| 2 | 4(18)* | 4(16)* | ND | 90 |
| 3 | 3(10) | ND | 2(10) | 50 |
| 4 | 3(18)* | .** | ND | 60+ |
| 5 | 5(12) | ND | 5(9) | 64 |

Notes:
*indicates sequences confirmed by sequencing of the V-genes of a hetero-hybridoma.
**the light chain PCR from this patient failed.
+Sample used was peripheral blood.
NLN = normal lymph node, SPL = spleen, ND = not done.

TABLE 3

Primers used to assemble vaccine constructs

| | | |
|---|---|---|
| VH3 scFv assembly primer | SEQ ID NO:67 | 5'-TCG CGG CCC AAC CGG CCA TGG CCC AGG TGC AGC TGC AGG AG-3' |
| VH4-34 scFv assembly primer | SEQ ID NO:68 | 5'-TCG CGG CCC AAC CGG CCA TGG CCC AGG TGC AGC TAC AGC AG-3' |
| CW 3'Linker primer | SEQ ID NO:69 | 5'-TTT CAT AGG TCC GGG TCC ACC TAG GAC GGT GAC CTT-3' |
| YJ 3'linker primer | SEQ ID NO:70 | 5'-TTT CAT AGG TCC GGG TCC ACC TAG GAC GGT CAG CTT-3' |
| WE 3'linker primer | SEQ ID NO:71 | 5'-TTT CAT AGG TCC GGG TCC TCG TTT GAT CTC CAC CTT-3' |
| Fragment C 5'linker primer | SEQ ID NO:72 | 5'-GGA CCC CGA CCT ATG AAA AAC CTT GATTGTTG-3' |
| Fragment C anti-sense primer | SEQ ID NO:73 | 5'-TAA TGC GGC CGC TTA GTC GTT GGT CCA ACC TTC-3' |

Restriction enzyme sites for cloning are underlined

TABLE 4

IgG subclass analysis of antibody responses

| Vaccine | Mice | Antigen | Antibody IgG subclass (ratios) | | |
|---|---|---|---|---|---|
| | | | $IgG_1$ | $IgG_{2a}$ | $IgG_{2b}$ |
| p.scFvYJ.FrC | 12 | FrC | 1.1 | 1 | 0.07 |
| | | YJIgM | 0.52 | 1 | 0.02 |
| p.scFvCW.FrC | 11 | FrC | 0.31 | 1 | 0.06 |
| | | CWIgM | 0.73 | 1 | 0.10 |
| p.scFvWE.FrC | 8 | FrC | 1.8 | 1 | 0.24 |
| | | WEIgM | 1.7 | 1 | 0.07 |
| YJIgM | 4 | YJIgM | 11.8 | 1 | 0.6 |

---

What is claimed is:

1. A nucleic acid construct encoding a fusion protein comprising an idiotypic determinant and fragment C of tetanus toxin.

2. The construct of claim 1, wherein the idiotypic determinant is expressed as an scFv.

3. The construct of claim 1, wherein the construct directs the synthesis of the fusion protein with an N-terminal leader sequence.

4. The construct of claim 1, comprising a sequence encoding the human $V_H$ 1 leader sequence.

5. The construct of claim 1, comprising at least one restriction endonuclease recognition site 5' and 3' of the sequence encoding the idiotypic determinant.

6. A method of making a nucleic acid construct according to claim 1, the method comprising:

(a) identifying a nucleic acid sequence encoding an idiotypic determinant present on a malignant B cell of a patient;

(b) cloning the nucleic acid sequence encoding the idiotypic determinant; and (c) introducing the cloned nucleic acid into a nucleic acid construct, which construct allows for the idiotypic determinant to be expressed as a fusion with fragment C of tetanus toxin.

7. The method of claim 6, wherein the cloning of step (b) comprises use of PCR.

8. The method of claim 6, wherein performance of the method results in a construct according to any one of claims 1 and 2–5.

* * * * *